(12) United States Patent
Li et al.

(10) Patent No.: US 12,150,670 B1
(45) Date of Patent: Nov. 26, 2024

(54) PET INTRAURETHRAL INCISION KNIFE

(71) Applicant: Li Li, Mingguang (CN)

(72) Inventors: Li Li, Mingguang (CN); Guowen Zhao, Mingguang (CN)

(73) Assignee: Li Li, Mingguang (CN)

( * ) Notice: Subject to any disclaimer, the term of this patent is extended or adjusted under 35 U.S.C. 154(b) by 0 days.

(21) Appl. No.: 18/767,070

(22) Filed: Jul. 9, 2024

(30) Foreign Application Priority Data

Aug. 31, 2023 (CN) .......................... 202311115069.4
Oct. 13, 2023 (CN) .......................... 202311325205.2

(51) Int. Cl.
*A61B 17/3209* (2006.01)
*A61B 17/3211* (2006.01)

(52) U.S. Cl.
CPC . *A61B 17/3209* (2013.01); *A61B 2017/32113* (2013.01)

(58) Field of Classification Search
CPC . A61D 1/00; A61D 1/02; A61D 99/00; A61B 17/3209; A61B 2017/32113
See application file for complete search history.

(56) References Cited

U.S. PATENT DOCUMENTS

| | | | | |
|---|---|---|---|---|
| 2,541,246 A * | 2/1951 | Held | ................ | A61B 17/32075 606/205 |
| 3,704,711 A * | 12/1972 | Park | ............... | A61B 17/320016 604/284 |
| 4,962,770 A * | 10/1990 | Agee | ............... | A61B 17/320036 128/898 |
| 4,963,147 A * | 10/1990 | Agee | ............... | A61B 17/320036 606/170 |
| 5,053,044 A * | 10/1991 | Mueller | ......... | A61B 17/320725 606/159 |
| 5,089,000 A * | 2/1992 | Agee | ............... | A61B 17/320036 606/170 |
| 5,306,284 A * | 4/1994 | Agee | ............... | A61B 17/320036 606/170 |
| 5,586,990 A * | 12/1996 | Hahnen | .......... | A61B 17/320016 606/167 |
| 5,601,572 A * | 2/1997 | Middleman | .......... | A61B 18/082 606/139 |
| 5,620,456 A * | 4/1997 | Sauer | .................. | A61B 17/3417 604/164.01 |
| 5,697,944 A * | 12/1997 | Lary | .................. | A61B 17/3209 606/159 |
| 7,429,264 B2 * | 9/2008 | Melkent | ............. | A61B 17/1671 606/159 |

(Continued)

*Primary Examiner* — Ryan J. Severson
(74) *Attorney, Agent, or Firm* — Birchwood IP

(57) ABSTRACT

Disclosed is a pet intraurethral incision knife, including a knife rod, a blade, and a guide wire, a blade slot is formed on one side of the knife rod, the hollow cavity is formed inside the knife rod in the length direction, the hollow cavity is communicated with the bottom of the blade slot, the blade can be rotationally retracted inside the blade slot, one end of the guide wire is abutted against an edge of one end of the blade, and the other end thereof passes through the hollow cavity and forms an operating end at one end of the knife rod, such that the operating end drives one end of the guide wire to push the blade to rotate and to be exposed from the opening of the blade slot, the blade can be hidden and stored inside the blade slot before being inserted into a pet urethra.

14 Claims, 17 Drawing Sheets

(56) References Cited

U.S. PATENT DOCUMENTS

| | | | | |
|---|---|---|---|---|
| 7,918,784 | B2* | 4/2011 | Wellborn | A61B 17/320036 600/149 |
| 8,840,631 | B2* | 9/2014 | Messmer | A61B 17/320016 606/167 |
| 9,028,474 | B2* | 5/2015 | Brannan | A61B 17/3211 606/33 |
| 9,364,259 | B2* | 6/2016 | Lunsford | A61B 17/3478 |
| 10,478,044 | B2* | 11/2019 | Yanuma | A61B 18/1492 |
| 10,499,942 | B2* | 12/2019 | Lown | A61B 17/320036 |
| 10,603,018 | B2* | 3/2020 | Wilson | A61B 17/00234 |
| 10,765,447 | B2* | 9/2020 | Laufer | A61B 17/320016 |
| 10,864,014 | B2* | 12/2020 | Laufer | A61B 17/320016 |
| 11,253,285 | B2* | 2/2022 | Fogg | A61B 17/320036 |
| 11,357,531 | B2* | 6/2022 | Lown | A61B 17/320036 |
| 11,974,769 | B2* | 5/2024 | Lown | A61B 17/320036 |
| 2005/0277968 | A1* | 12/2005 | Lee | A61B 17/320016 606/170 |
| 2007/0225740 | A1* | 9/2007 | Suddaby | A61B 17/3211 606/170 |
| 2008/0045989 | A1* | 2/2008 | Welborn | A61B 17/320036 606/170 |
| 2009/0187203 | A1* | 7/2009 | Corvi | A61B 17/320783 606/159 |
| 2010/0268175 | A1* | 10/2010 | Lunsford | A61B 17/320725 604/272 |
| 2011/0238053 | A1* | 9/2011 | Brannan | A61B 18/1815 606/33 |
| 2012/0150208 | A1* | 6/2012 | Messmer | A61B 17/320016 606/167 |
| 2015/0217100 | A1* | 8/2015 | Karino | A61F 2/82 606/167 |
| 2015/0342633 | A1* | 12/2015 | Yanuma | A61B 18/1492 606/127 |
| 2016/0015415 | A1* | 1/2016 | Wolff | A61B 17/320016 606/171 |
| 2016/0166243 | A1* | 6/2016 | Wilson | A61B 17/00234 606/190 |
| 2016/0206345 | A1* | 7/2016 | Laufer | A61B 18/1492 |
| 2017/0164968 | A1* | 6/2017 | Laufer | A61B 17/320016 |
| 2018/0125950 | A1* | 5/2018 | Khan | A61B 17/3209 |
| 2020/0305918 | A1* | 10/2020 | Fogg | A61B 17/32002 |
| 2022/0047293 | A1* | 2/2022 | Sadlouparizi | A61B 17/320036 |
| 2022/0167954 | A1* | 6/2022 | McGovern | A61B 17/00008 |

* cited by examiner

PET INTRAURETHRAL INCISION KNIFE

CROSS-REFERENCE TO RELATED APPLICATIONS

This application claims priority to Chinese Patent Application No. 202311115069.4, filed on Aug. 31, 2023 and Chinese Patent Application No. 202311325205.2, filed on Oct. 13, 2023, which is hereby incorporated by reference in its entirety.

TECHNICAL FIELD

The present disclosure relates to the technical field of medical devices for pets, particularly relates to a pet intraurethral incision knife.

BACKGROUND

At present, urinary retention caused by urethral stricture is one of the most common urological diseases in the field of pet clinical medicine, especially a male cat has relatively a narrow urethra, once suffering from the urinary retention, the male cat may die within a few days, with a very high mortality rate. The main causes of urinary retention in pets include: (1) stones or crystals blocking the urethra or ureter; (2) spontaneous cystitis; (3) urinary tract infection; (4) stress-induced urinary retention, among others. For the treatment of urinary retention in pets, traditional methods include urethrostomy or oral medication. However, the traditional methods of urethrostomy have many sequelae, while oral medication is slow to take effect.

In the prior art, there are also solutions that use intraurethral incision knives for surgical operation. an intraurethral incision knife, including a cylindrical hollow knife rod, with a guide wire running through an interior of the knife rod; a curved blade is disposed on one side of the knife rod, the knife rod and the curved blade form an integral structure, and the blade is disposed on the one side of the knife rod in a protruding manner. Outward protrusion and fixation of the blade relative to the knife rod increases an overall width of the intraurethral incision knife, therefore, a doctor needs to be particularly careful when inserting the intraurethral incision knife into the narrow urethra of the pet to avoid cutting healthy parts of the urethra. Moreover, the surgical operation must be slowed down, otherwise, when the straight and rigid knife rod and blade are quickly inserted into the narrow urethra of the pet, the urethra will be easily scratched, making the surgical cutting operation more difficult, and resulting inconvenient use of the intraurethral incision knife.

SUMMARY

An objective of the present disclosure is to provide a pet intraurethral incision knife, so as to solve the technical problems of difficult operation and inconvenient use of the pet intraurethral incision knives in the prior art.

In order to achieve the above objectives, a technical solution of the present disclosure provides a pet intraurethral incision knife, including:

a knife rod, a blade slot is formed on one side of the knife rod, a hollow cavity is formed inside the knife rod in a length direction, and the hollow cavity is communicated with a bottom of the blade slot, and the knife rod is a flexible soft rod structure;

a blade, the blade is rotationally retracted inside the blade slot, and the blade has a retracted state and an exposed state relative to the blade slot; and a guide wire, one end of the guide wire is abutted against an edge of one end of the blade, and the other end of the guide wire passes through a hollow cavity and forms an operating end at one end of the knife rod, such that the operating end drives one end of the guide wire to push the blade to rotate and to be exposed from an opening of the blade slot, and the blade can be switched from the retracted state to the exposed state.

In some embodiments, an inclined surface is disposed at the edge of one end of the blade, and when the blade in the exposed state, the blade is abutted against one end of the guide wire through the inclined surface to support the blade for positioning.

In some embodiments, when the blade is in the retracted state, the blade is retracted inside the blade slot, a length direction of the blade is parallel to a longitudinal axis of the knife rod, and the inclined surface is inclined to the longitudinal axis of the knife rod; and when the blade is in the exposed state, the other end of the blade is exposed from the opening of the blade slot, the length direction of the blade is inclined to the longitudinal axis of the knife rod, and the inclined surface is parallel to the longitudinal axis of the knife rod.

In some embodiments, the blade slot is disposed in a way of extending in the length direction of the knife rod, one end of the blade can be rotationally mounted inside the blade slot through a pivot shaft, and the pivot shaft is extended in a width direction of the blade slot.

In some embodiments, further comprising a mounting rod, wherein a mounting groove is formed on one side of the mounting rod, the mounting groove is disposed correspondingly to the blade slot, and mounting holes are formed on two opposite side walls of the mounting groove, such that the blade is inserted into the mounting groove and is inserted into the through hole of the blade through the pivot shaft, two ends of the pivot shafts are respectively inserted into two mounting holes to make the blade capable of being rotationally mounted, and the mounting rod is then inserted into the hollow cavity of the knife rod to make the mounting groove of the mounting rod disposed correspondingly to the blade slot.

In some embodiments, a penetrating hole is formed inside the mounting rod in a length direction, the penetrating hole is communicated with a bottom of the mounting groove, and one end of the guide wire is movably inserted into the penetrating hole; and when the blade is in the retracted state, the blade at least partially passes through the bottom of the mounting groove and is abutted against the guide wire inside the penetrating hole, such that the guide wire can push the blade to rotate and to be exposed from the opening of the blade slot.

In some embodiments, further comprising a pushing member, the pushing member is movably disposed inside the hollow cavity of the knife rod, and one end of the guide wire is connected to the pushing member, such that one end of the guide wire is abutted against the edge of one end of the blade through the pushing member, and the operating end drives the guide wire to drive the pushing member to push the blade to rotate and to be exposed from the opening of the blade slot.

In some embodiments, the blade slot is disposed in a way of extending in the length direction of the knife rod, the other end of the blade can be rotationally mounted inside the blade slot through the pivot shaft, and a pivot axis of the pivot shaft is extended in the width direction of the blade slot.

In some embodiments, further comprising the mounting rod, the mounting groove is formed on a side of the mounting rod facing the opening of the blade slot in a length direction, such that the other end of the blade can be rotationally mounted inside the mounting groove through the pivot shaft, and the mounting rod is inserted into the hollow cavity of the knife rod to make the blade rotationally mounted inside the blade slot.

In some embodiments, a guide surface is disposed at the edge of one end of the blade, a guide groove is formed on one end of the pushing member close to the blade, and one end of the blade is movably disposed in the guide groove through the guide surface, such that the pushing member is abutted against the guide surface through the guide groove and pushes the blade to rotate and to be exposed from the opening of the blade slot.

In some embodiments, further comprising the mounting rod, the mounting groove is formed on the side of the mounting rod facing the opening of the blade slot in the length direction, the other end of the blade can be rotationally mounted inside the mounting groove through the pivot shaft, the penetrating hole is formed inside the mounting rod in the length direction, the penetrating hole is communicated with the bottom of the mounting groove, the pushing member is movably disposed inside the penetrating hole, and one end of the guide wire is inserted into the penetrating hole and is connected to the pushing member, such that the mounting rod is inserted into the hollow cavity of the knife rod to make the blade rotationally mounted inside the blade slot; and when the blade is in the retracted state, the blade at least partially passes through the bottom of the mounting groove and is abutted against the pushing member inside the penetrating hole, such that the guide wire can push the blade through the pushing member to rotate and to be exposed from the opening of the blade slot.

In some embodiments, further comprising a rod handle and a driving member, wherein the rod handle is disposed at one end of the knife rod, the driving member is movably disposed on the rod handle, and the driving member is in driving connection with the operating end of the guide wire, such that the driving member drives the guide wire to push the blade to be exposed from the opening of the blade slot.

In some embodiments, the driving member comprises a rotating member, the rotating member is in threaded connection with the rod handle, and the rotating member is connected to the operating end of the guide wire, such that the guide wire is driven to push the blade to rotate and to be exposed from the opening of the blade slot by rotating the rotating member; or the driving member comprises a sliding block, the sliding block is connected to the operating end of the guide wire, a sliding portion is disposed on at least one side of the sliding block, a guide slot is formed on the rod handle in a length direction, and the sliding portion is slidably disposed in the guide slot, such that the guide wire can be driven to push the blade to be exposed from the opening of the blade slot by manually pushing and pulling the sliding block.

In some embodiments, further comprising the rod handle and the driving member, and the rod handle is disposed at one end of the knife rod; and the driving member comprises the rotating member, the rotating member is in threaded connection with the rod handle, and the rotating member is connected to the operating end of the guide wire, a threaded hole is formed on the pushing member in a length direction, one end of the guide wire is threadedly connected in the threaded hole, and the pushing member is inserted into the hollow cavity of the knife rod in a non-rotational manner, such that the guide wire is driven to bring the pushing member to move by rotating the rotating member; or further comprising the rod handle and the driving member, and the rod handle is disposed at one end of the knife rod; and the driving member comprises a sliding block, the sliding block is connected to the operating end of the guide wire, the sliding portion is disposed on at least one side of the sliding block, the guide slot is formed on the rod handle in the length direction, and the sliding portion is slidably disposed in the guide slot, such that the guide wire is driven to bring the pushing member to move by pushing and pulling the sliding block; or further comprising the rod handle and the driving member, and the rod handle is disposed at one end of the knife rod; and the driving member comprises the rotating member and the sliding block, the sliding block is connected to the operating end of the guide wire, the sliding portion is disposed on at least one side of the sliding block, the guide slot is formed on the rod handle in the length direction, the sliding portion is slidably disposed in the guide slot, the rotating member is in threaded connection with the rod handle, and the rotating member is abutted against the sliding block, such that the sliding block can be driven to bring the pushing member to move by rotating the rotating member to push the sliding block to slide.

It can be seen from the above technical solution that the pet intraurethral incision knife provided in in the present disclosure includes the knife rod, the blade, and the guide wire, the blade slot is formed on one side of the knife rod, the hollow cavity is formed inside the knife rod in the length direction, the hollow cavity is communicated with the bottom of the blade slot, the blade can be rotationally retracted inside the blade slot, the blade has the retracted state and the exposed state relative to the blade slot, one end of the guide wire is abutted against the edge of one end of the blade, and the other end of the guide wire passes through the hollow cavity and forms the operating end at one end of the knife rod, such that the operating end drives one end of the guide wire to push the blade to rotate and to be exposed from the opening of the blade slot, and the blade is switched from the retracted state to the exposed state, in this way, the blade can be hidden and stored inside the blade slot before the pet intraurethral incision knife is inserted into the pet urethra to prevent the blade from scratching normal parts of the pet urethra, and the knife rod can be inserted into the pet urethra more smoothly; and when the blade reaches the narrow blocking part of the pet urethra, the guide wire is driven by the operating end to push the blade to be exposed from the opening of the blade slot and perform surgical cutting on the narrow blocking part of the pet urethra. Therefore, the pet intraurethral incision knife features simple structural design, makes the operation more convenient, thereby effectively reducing the difficulty of surgical operation.

In order to make the technical concept and other objects, advantages, features and effects of the present disclosure clearer and more comprehensible, preferred embodiments will be specifically cited in the following specific implementation modes and described in detail in conjunction with the accompanying drawings.

BRIEF DESCRIPTION OF DRAWINGS

In order to illustrate the technical solution in embodiments of the present disclosure more clearly, the following briefly introduces accompanying drawings used in the description of the embodiments. Obviously, the accompanying drawings in the following description are only some embodiments of the present disclosure. Those of ordinary skill in the art can obtain other accompanying drawings from these accompanying drawings without any creative efforts.

Figure 1:
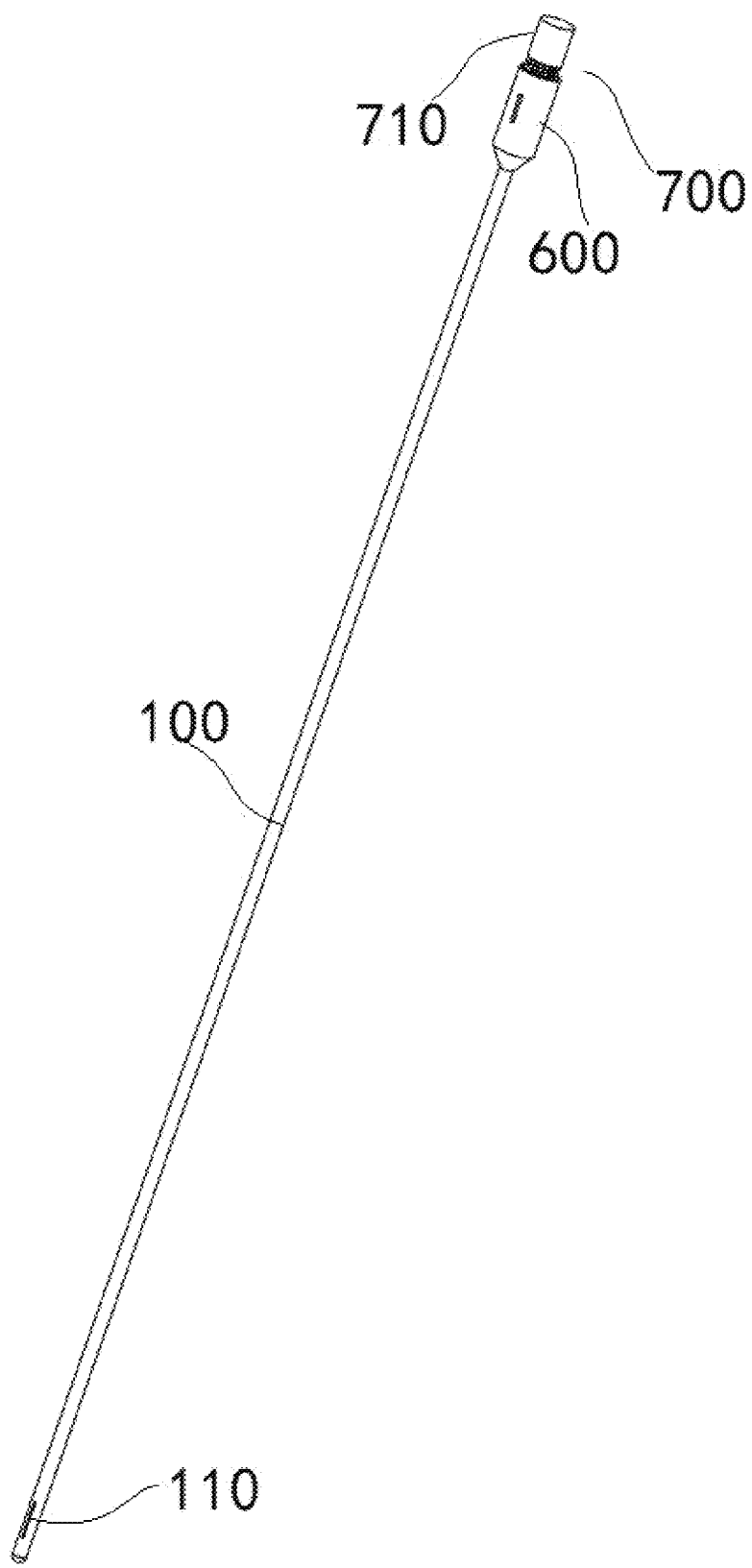
FIG. 1 is a structural schematic diagram of a pet intraurethral incision knife in a retracted state according to an implementation mode of an embodiment in the present disclosure.
Figure 2:
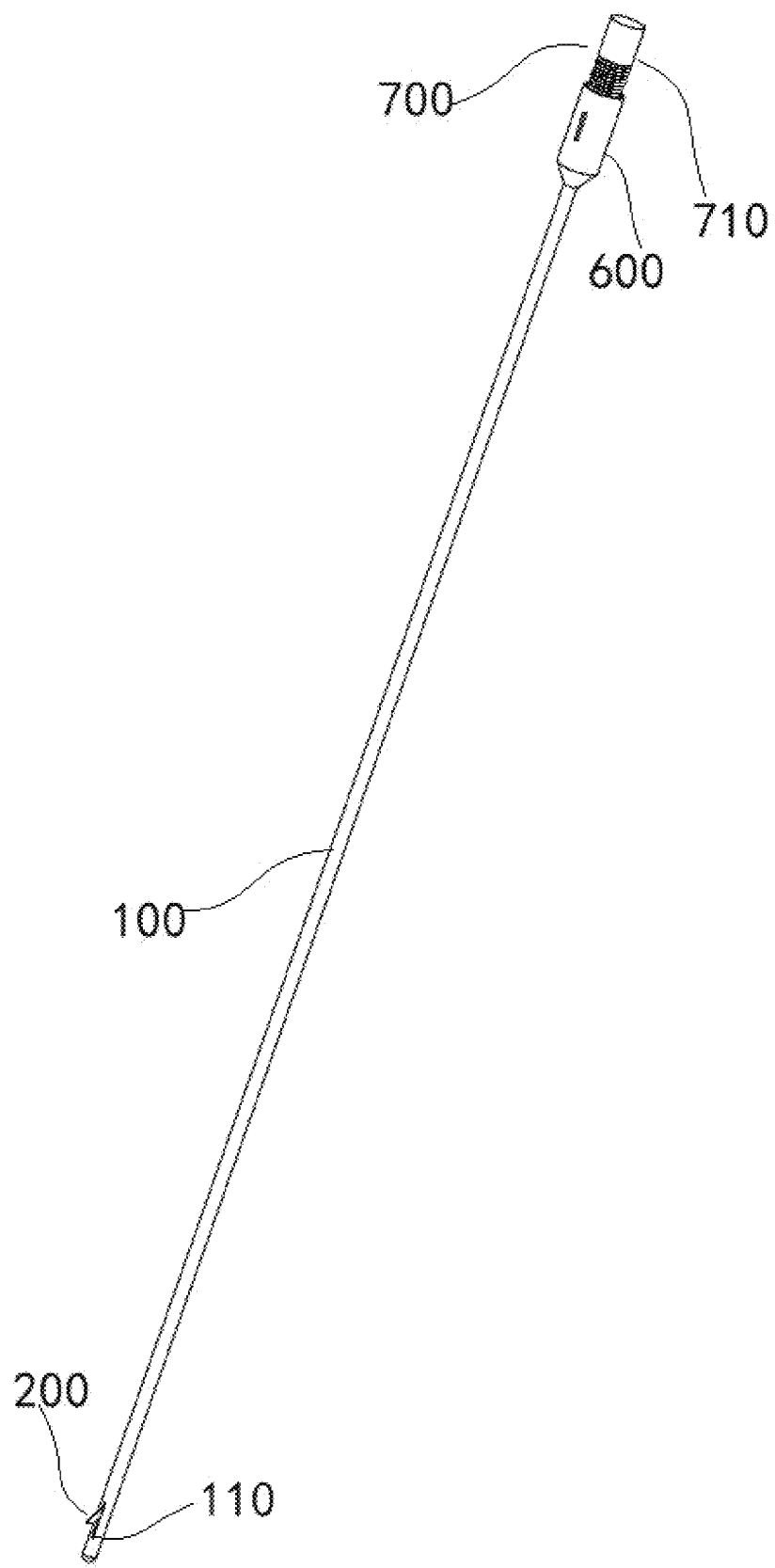
FIG. 2 is a structural schematic diagram of a pet intraurethral incision knife in an exposed state according to an implementation mode of an embodiment in the present disclosure.
Figure 3:
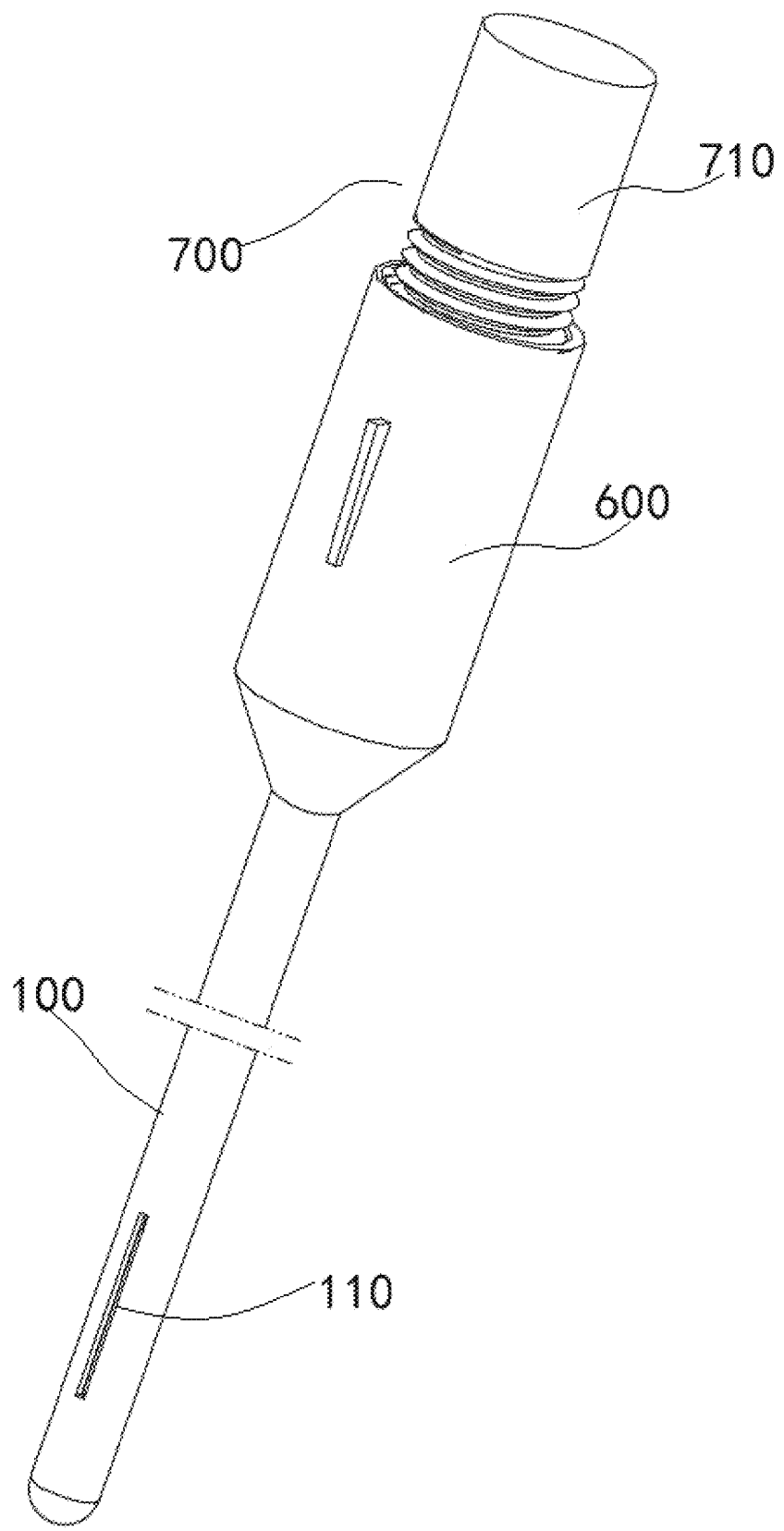
FIG. 3 is a simplified schematic diagram of a pet intraurethral incision knife in a retracted state according to an implementation mode of an embodiment in the present disclosure.
Figure 4:
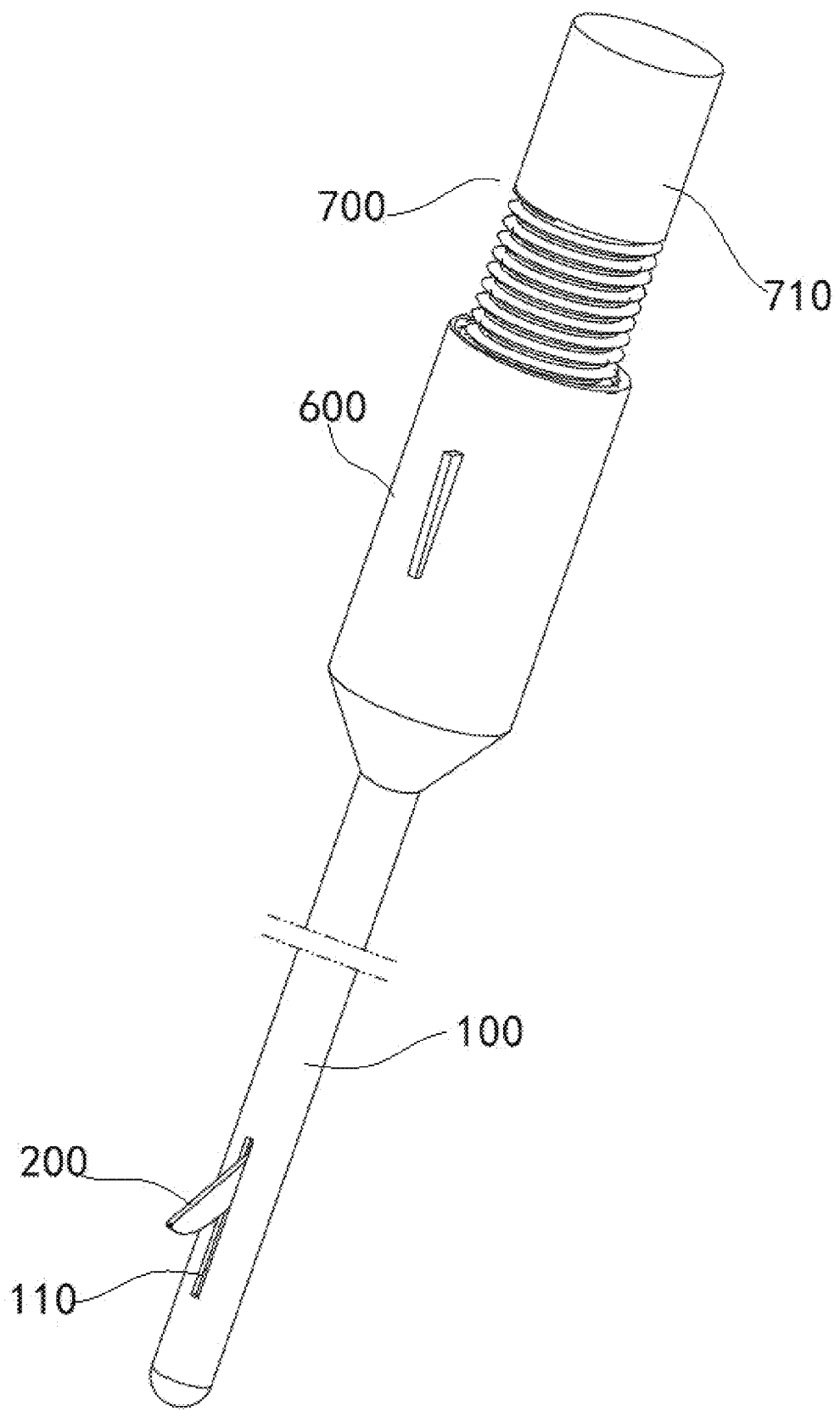
FIG. 4 is a simplified schematic diagram of a pet intraurethral incision knife in an exposed state according to an implementation mode of an embodiment in the present disclosure.

The above figures includes the following reference numerals:

100. knife rod; 110. blade slot; 120. hollow cavity; 130. end cap; 200. blade; 210. through hole; 220. guide surface; 230. first end; 240. second end; 250. inclined surface; 300. pushing member; 310. guide groove; 320. threaded hole; 400. guide wire; 500. mounting rod; 510. mounting groove; 520. mounting hole; 530. penetrating hole; 600. rod handle; 610. guide wall; 611. guide slot; 700. driving member; 710. rotating member; 720. sliding block; and 721. sliding portion.

DETAILED DESCRIPTION OF THE EMBODIMENTS

In the embodiment of the present disclosure, a pet intraurethral incision knife is provided to solve the technical problems of difficult operation and inconvenient use of the pet intraurethral incision knives in the prior art. A blade slot 110 is formed on one side of a knife rod 100, such that a blade 200 can be hidden and stored in the blade slot 110 in the process of inserting the pet intraurethral incision knife into a pet urethra, and the knife rod 100 and the blade 200 can be inserted into the pet urethra more smoothly; and when the blade 200 reaches a narrow blocking part of the pet urethra, a guide wire 400 is driven by an operating end to drive a pushing member 300 to push the blade 200 to be exposed from an opening of the blade slot 110 and perform surgical cutting on the narrow blocking part of the pet urethra, which is convenient to use and easy to operate.

In order to make those skilled in the art better understand the technical solution of the present disclosure, the technical solution in the embodiments of the present disclosure will be clearly and completely described below with reference to accompanying drawings in the embodiments of the present disclosure. Obviously, the described embodiments are only a part of the embodiments of the present disclosure, but not all of the embodiments. Based on the embodiments of the present disclosure, all other embodiments obtained by those skilled in the art without any creative efforts fall within the protection scope of the present disclosure.

With reference to FIGS. 1-17, this embodiment provides a pet intraurethral incision knife, including the knife rod 100, the blade 200, and the guide wire 400, the blade slot 110 is formed on one side of the knife rod 100, a hollow cavity 120 is formed inside the knife rod 100 in a length direction, the hollow cavity 120 is communicated with a bottom of the blade slot 110, the blade 200 can be rotationally retracted inside the blade slot 110, the blade 200 has a retracted state and an exposed state relative to the blade slot 110, one end of the guide wire 400 is abutted against an edge of one end of the blade 200, and the other end of the guide wire 400 passes through the hollow cavity 120 and forms the operating end at one end of the knife rod 100, such that the operating end drives one end of the guide wire 400 to push the blade 200 to rotate and to be exposed from the opening of the blade slot 110, and the blade 200 is switched from the retracted state to the exposed state, where the knife rod 100 can adopt a slender hollow rod structure, the guide wire 400 can be movably inserted into the knife rod 100, the blade 200 can be exposed from the opening of the blade slot 110 by pulling the guide wire 400 by hand to drive the pushing member 300 to push the blade 200 titled upwards, and the blade 200 has a cutting edge on a side facing the opening of the blade slot 110, so as to facilitate surgical cutting of the narrow blocking part of the pet urethra; when the blade 200 is in the retracted state, the knife rod 100 can be inserted into a narrow urethra of a pet smoothly; and when the blade 200 is in the exposed state, the blade 200 can conveniently cut the narrow blocking part of the pet urethra.

As shown in FIGS. 1-2 and FIGS. 8-9, it can be seen that the pet intraurethral incision knife provided in this embodiment includes the knife rod 100, the blade 200, and the guide wire 400, the blade slot 110 is formed on one side of the knife rod 100, the hollow cavity 120 is formed inside the knife rod 100 in the length direction, the hollow cavity 120 is communicated with the bottom of the blade slot 110, the blade 200 can be rotationally retracted inside the blade slot 110, the blade 200 has the retracted state and the exposed state relative to the blade slot 110, one end of the guide wire 400 is abutted against the edge of one end of the blade 200, and the other end of the guide wire 400 passes through the hollow cavity 120 and forms the operating end at one end of the knife rod 100, such that the operating end drives one end of the guide wire 400 to push the blade 200 to rotate and to be exposed from the opening of the blade slot 110, and the blade 200 is switched from the retracted state to the exposed state, in this way, the blade 200 can be hidden and stored inside the blade slot 110 before the pet intraurethral incision knife is inserted into the pet urethra to prevent the blade 200 from scratching normal parts of the pet urethra, and the knife rod 100 can be inserted into the pet urethra more smoothly; and when the blade 200 reaches the narrow blocking part of the pet urethra, the guide wire 400 is driven by the operating end to push the blade 200 to be exposed from the opening of the blade slot 110 and perform surgical cutting on the narrow blocking part of the pet urethra. Therefore, the pet intraurethral incision knife features simple structural design, makes the operation more convenient, thereby effectively reducing the difficulty of surgical operation and improving the efficiency of surgical cutting.

In one embodiment, as shown in FIGS. 5-7 and FIGS. 12-14, the pet intraurethral incision knife further includes the pushing member 300, the pushing member 300 is movably disposed inside the hollow cavity 120 of the knife rod 100, and one end of the guide wire 400 is connected to the pushing member 300, such that one end of the guide wire 400 is abutted against the edge of one end of the blade 200 through the pushing member 300, and the operating end drives the guide wire 400 to drive the pushing member 300 to push the blade 200 to rotate and to be exposed from the opening of the blade slot 110.

In this embodiment, as shown in FIGS. 5-7 and FIGS. 12-14, a first end 230 of the blade 200 is pivotally connected to the knife rod 100, and a second end 240 of the blade 200 is abutted against the pushing member 300, such that the blade 200 is pushed by the pushing member 300 to be exposed from the opening of the blade slot 110 in a way of rotating around a pivot shaft; since the pet urethra is very narrow, in order to make the pet intraurethral incision knife be inserted into the pet urethra more smoothly, the knife rod 100 usually adopts the slender hollow rod structure, with an outer diameter being approximately 1-1.5 mm, and an inner diameter of the hallow cavity 120 is less than 1.0 mm, therefore, a space of the hollow cavity 120 inside the knife rod 100 is very narrow. The inventors found in the process of implementing tests that when one end of the guide wire 400 is directly connected to one end of the blade 200 in the way of some existing large-sized medical knives of the other industries, the space of the hollow cavity 120 inside the knife rod 100 is relatively narrow due to a very narrow pet urethra, as a result, the blade 200 does not have enough movable space to push the blade 200 to tilt upwards when the blade is rotationally connected to one end of the guide wire 400, or a height at which the blade 200 tilts upwards from the blade slot 110 is relatively low, failing to meet basic requirements, and resulting in poor surgical cutting effect. In this embodiment, one end of the guide wire 400 is detachable abutted against the edge of one end of the blade 200, and the guide wire 400 is not directly connected to the blade 200 in a rotational manner, such that the operating end can pull and push the guide wire to move inside the knife rod 100 in the length direction and drive the blade 200 to rotate and tilt upwards from the blade slot 110, in this way, the blade 200 adopts the mode of tilting upwards through pushing, making the pet intraurethral incision knife have better use effect, being easier to implement in industrial manufacturing, featuring simple structural design and reducing the processing difficulty and production costs.

Specifically, as shown in FIGS. 5-7 and FIGS. 12-14, the blade slot 110 is disposed in a way of extending in the length direction of the knife rod 100, the first end 230 of the blade 200 can be rotationally mounted inside the blade slot 110 through the pivot shaft, a pivot axis of the pivot shaft is extended in a width direction of the blade slot 110, and the pivot shaft can be a pivot pin or a metal wire, where the pushing member 300 is movably inserted into the hollow cavity 120 of the knife rod 100, such that the pushing member 300 is driven by pushing and pulling the guide wire 400 to move in the length direction of the knife rod 100, and to push the blade 200 to be exposed from the opening of the blade slot 110 in a rotating manner.

Further, as shown in FIGS. 5-7 and FIGS. 12-14, the pet intraurethral incision knife further includes a mounting rod 500, a mounting groove 510 is formed on a side of the mounting rod 500 facing the opening of the blade slot 110 in the length direction, and one end of the mounting groove 510 close to the blade 200 is provided with an opening, such that the first end 230 of the blade 200 can be rotationally disposed in the mounting groove 510 by means of the pivot shaft, the mounting rod 500 is inserted into the hollow cavity 120 of the knife rod 100, the blade 200 can be rotationally mounted inside the blade slot 110, where the knife rod 100 is a flexible rod structure, and in this embodiment, the blade 200 is mounted by inserting the mounting rod 500 into the knife rod 100, which effectively improves the stability, reliability and seclusion of a mounting structure of the blade 200.

Specifically, as shown in FIGS. 5-7 and FIGS. 12-14, the mounting rod 500 is roughly cylindrical, mounting holes 520 are formed on two opposite side walls of the mounting groove 510 in a width direction, and a through hole 210 is formed on the first end 230 of the blade 200; in the assembly process, the first end 230 of the blade 200 can be first inserted into the mounting groove 510, and then pass through the mounting holes 520 on the two side walls of the mounting groove 510 and the through hole 210 of the blade 200, such that the blade 200 can be rotationally mounted on the mounting rod 500, the mounting rod 500 and the blade 200 are inserted into the hollow cavity 120 from one end portion of the knife rod 100, and the blade 200 is disposed correspondingly to the blade slot 110; preferably, the blade slot 110 is disposed adjacent to the other end of the knife rod 100, such that the blade 200 is correspondingly assembled into the blade slot 110, and specifically, a penetrating hole 530 is formed inside the mounting rod 500 in a length direction thereof for the guide wire 400 to pass through.

Figure 5:
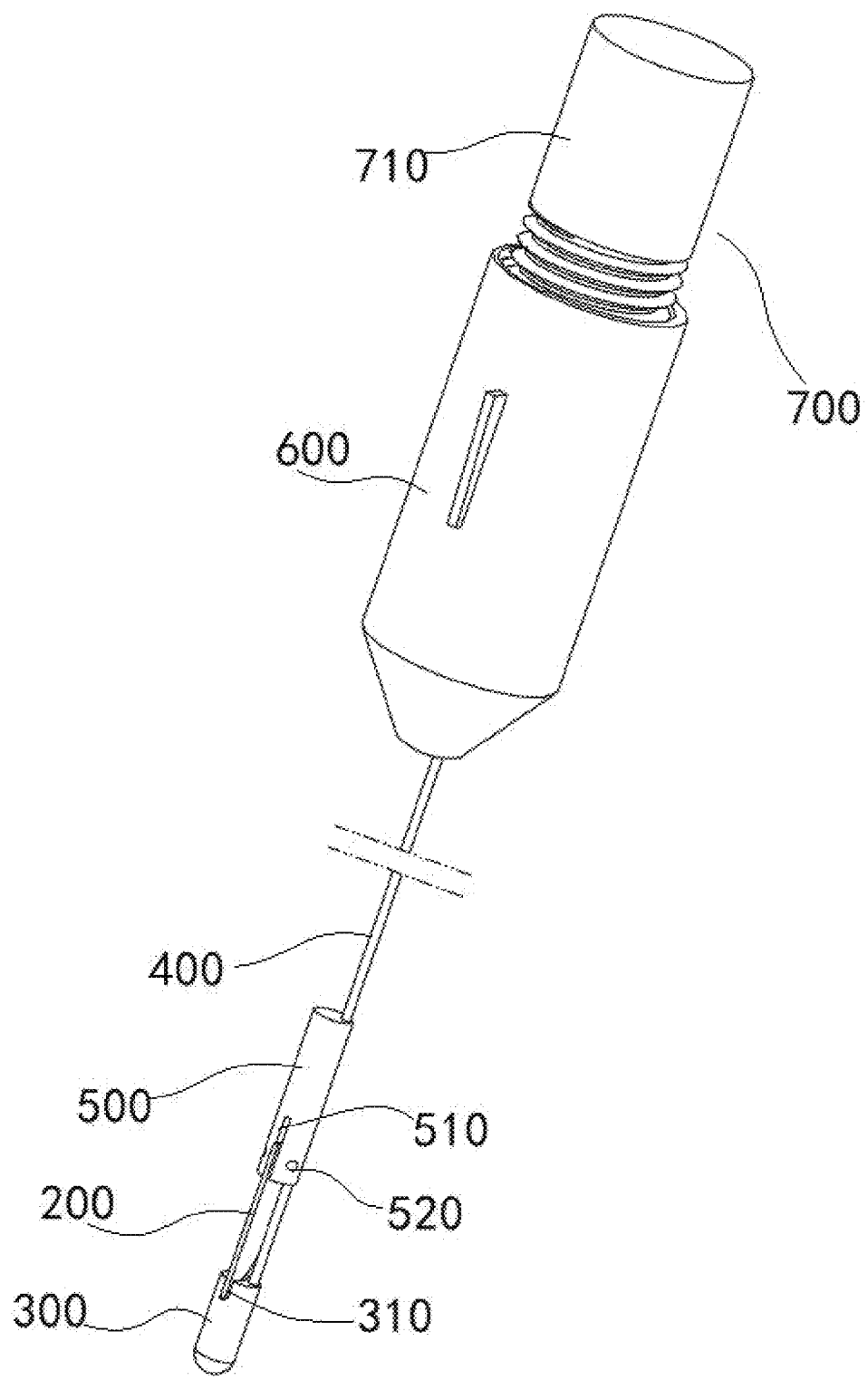
FIG. 5 is a simplified schematic diagram of FIG. 3 according to the embodiment in the present disclosure after the knife rod is omitted.
Figure 6:
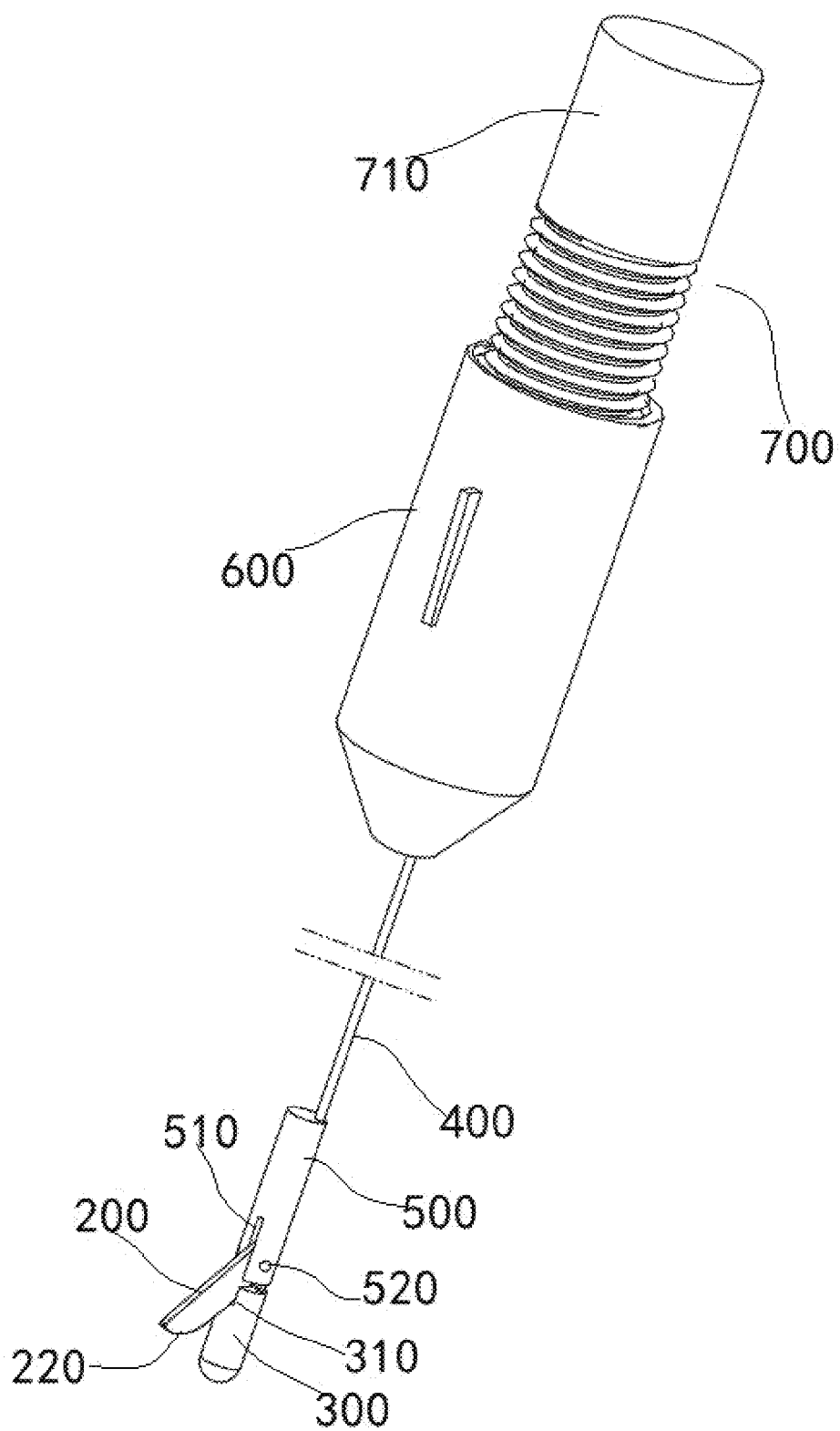
FIG. 6 is a simplified schematic diagram of FIG. 4 according to the embodiment in the present disclosure after the knife rod is omitted.
Figure 12:
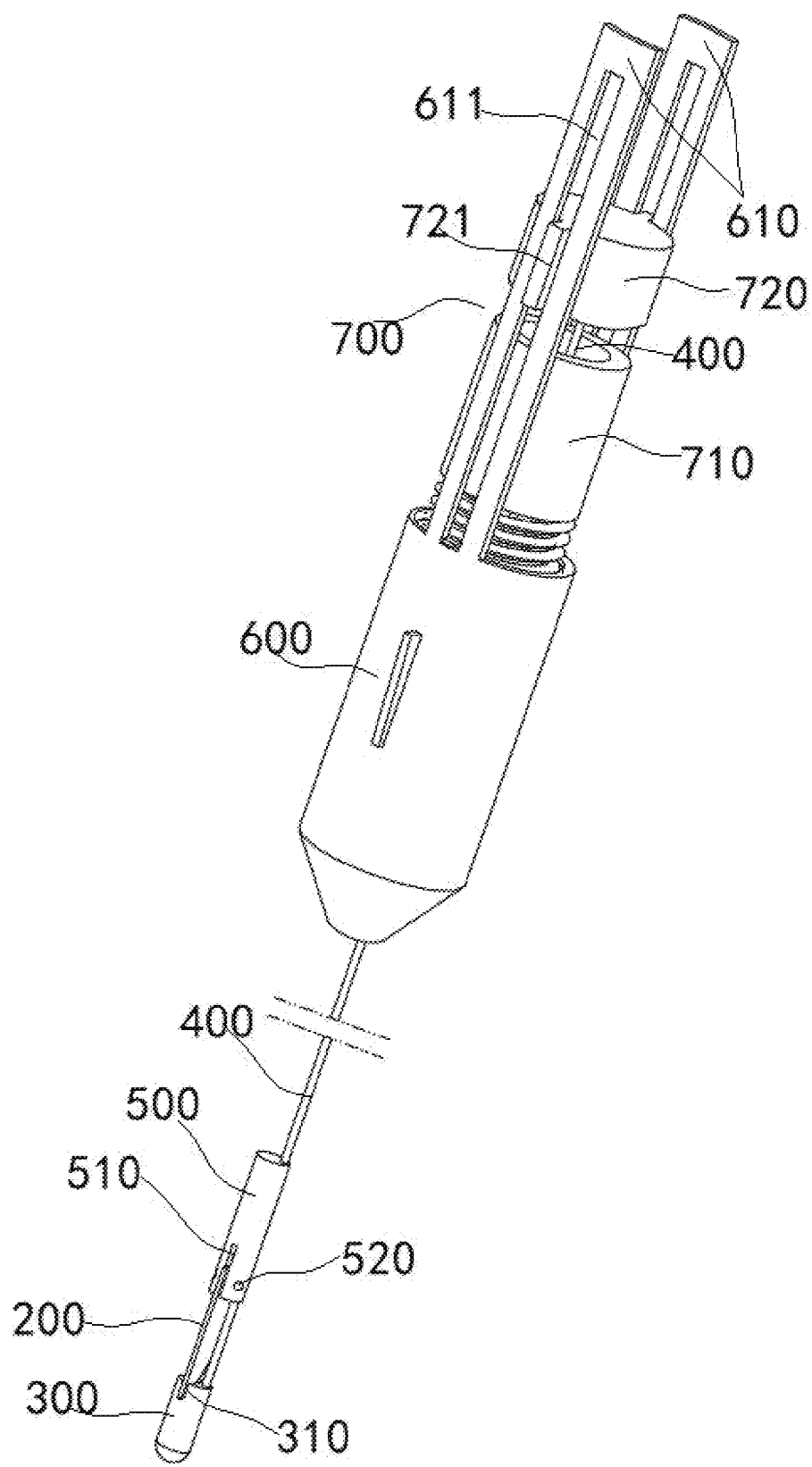
FIG. 12 is a simplified schematic diagram of FIG. 10 according to the embodiment in the present disclosure after the knife rod is omitted.
Figure 13:
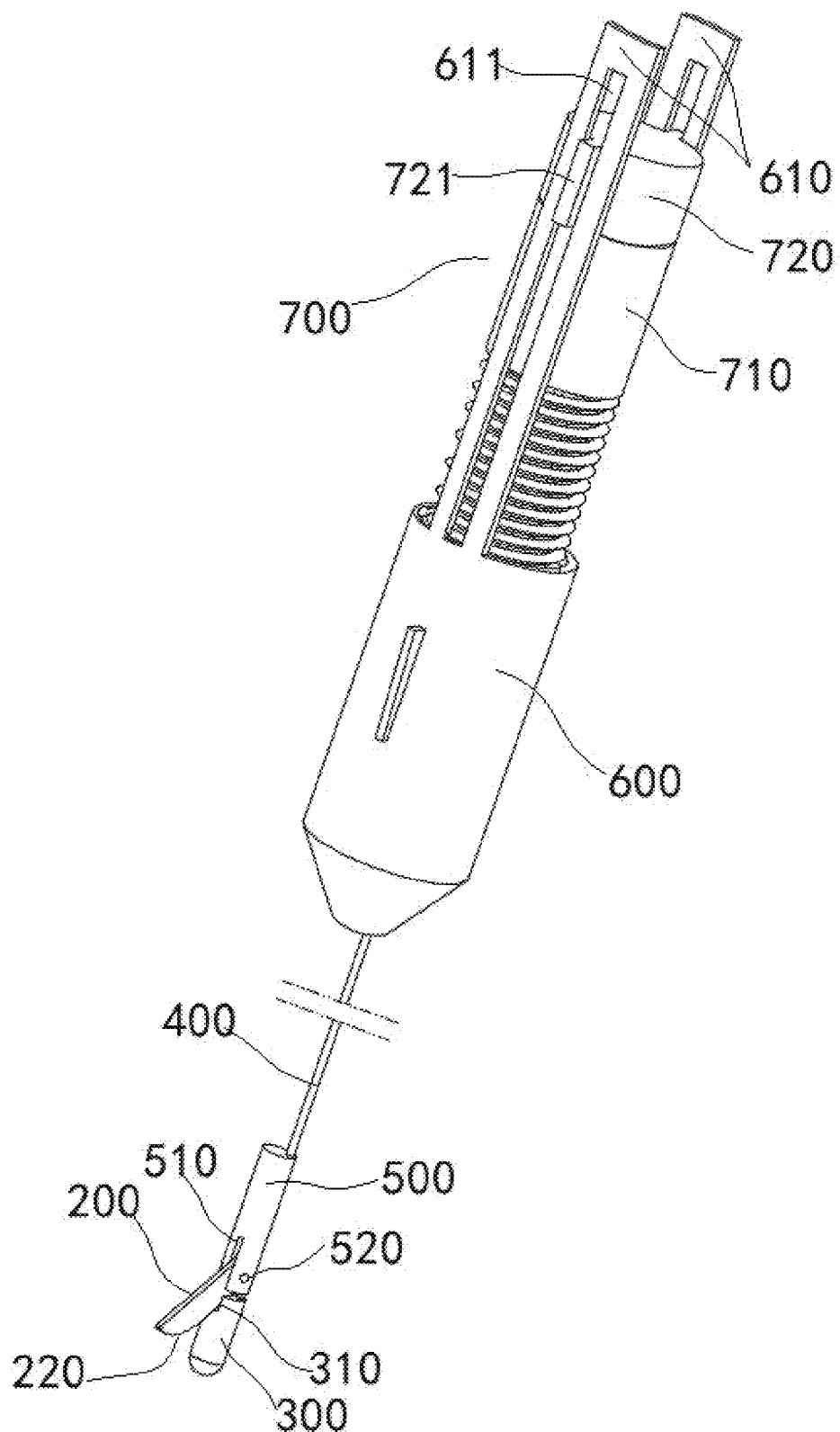
FIG. 13 is a simplified schematic diagram of FIG. 11 according to the embodiment in the present disclosure after the knife rod is omitted.

In this embodiment, as shown in FIGS. 5-7 and FIGS. 12-14, the second end 240 of the blade 200 is provided with a guide surface 220, a guide groove 310 is formed on one end of the pushing member 300 close to the blade 200, a side of the guide groove 310 facing the opening of the blade slot 110 is provided with an opening, and the second end 240 of the blade 200 is movably disposed in the guide groove 310 through the guide surface 220, such that the pushing member 300 drives through cooperation between the guide groove 310 and the guide surface 220 to drive the blade 200 to be exposed from the opening of the blade slot 110 in a way of rotating around the pivot shaft; specifically, in the assembly process, the pushing member 300 is first connected to one end of the guide wire 400, the pushing member 300 is inserted into the hollow cavity 120 from the other end of the knife rod 100, such that the guide groove 310 is disposed correspondingly to the guide surface 220 of the second end 240 of the blade 200, and finally, an end cap 130 is covered on the hollow cavity 120 at the other end of the knife rod 100; specifically, a slot bottom of the blade slot 110 is communicated with the hollow cavity 120, and the blade 200 is located between the pushing member 300 and the mounting rod 500; and as shown in FIGS. 6 and 13, when the blade 200 is in the exposed state, the blade 200 is tightly clamped and fixed, and tilted upwards from the opening of the blade slot 110 through cooperation between the guide groove 310 of the pushing member 300 and the mounting groove 510 of the mounting rod 500.

As shown in FIGS. 5-7 and FIGS. 12-14, preferably, the guide surface 220 is a curved surface, and a bottom wall surface of the guide groove 310 is adapted to the guide surface 220, such that a motion mode of the pushing member 300 is converted into a rotational movement mode of the blade 200 through the cooperation between the guide groove 310 and the guide surface 220, which is more stable and reliable, has a compact structural design, and effectively improves the stability and reliability of the structural design.

In other embodiments, the pushing member 300 can be mounted inside the mounting rod 500 and mounted together with the mounting rod 500 inside the hollow cavity 120 of the knife rod 100; specifically, the mounting groove 510 is formed on the side of the mounting rod 500 facing the opening of the blade slot 110 in the length direction thereof, the other end of the blade 200 is rotationally disposed in the mounting groove 510 through the pivot shaft, the penetrating hole 530 is formed inside the mounting rod 500 in the length direction thereof, the penetrating hole 530 is communicated with a bottom of the mounting groove 510, the pushing member 300 is movably disposed in the penetrating hole 530, and one end of the guide wire 400 is inserted into the penetrating hole 530 and is connected to the pushing member 300, such that the blade 200 can be rotationally mounted inside the blade slot 110 by inserting the mounting rod 500 into the hollow cavity of the knife rod 100; and when the blade 200 is in the retracted state, the blade 200 at least partially passes through the bottom of the mounting groove 510 and is abutted against the pushing member 300 in the penetrating hole 530, such that the guide wire 400 can push the blade 200 to rotate through the pushing member 300 and to be exposed from the opening of the blade slot 110.

The mounting rod 500 and an inner wall of the hollow cavity 120 of the knife rod 100 can be bonded and fixed with glue, or an inner wall of the knife rod 100 can be contracted by means of a hot melting process to be tightly fitted and fixed with the mounting rod 500, featuring a simple and compact structural design, facilitating production and assembly, and effectively improving the stability and reliability of the structural design.

In this embodiment, as shown in FIGS. 1-2 and FIGS. 8-9, the knife rod 100 is a slender and flexible soft rod structure, the soft rod structure is preferably made of PVC or PE soft plastic material, the guide wire 400 is made of metal material, and guide wire 400 is inserted into the soft rod structure to provide skeletal support, or the knife rod 100 is segmented and is composed of a soft rod portion and a hard rod portion to form the slender knife rod 100, where the soft rod portion is made of soft plastic material, the hard rod portion is made of hard plastic or metal material, and the soft rod structure or the soft rod portion has a soft adaptive bending characteristic, such that the knife rod 100 can be inserted into the pet urethra more smoothly through the soft characteristics of the knife rod 100 to adapt to bending changes of the pet urethra, avoiding scratching the pet urethra with a straight hard rod structure.

In this embodiment, as shown in FIGS. 5-7 and FIGS. 12-14, the pet intraurethral incision knife further includes a rod handle 600 and a driving member 700, the rod handle 600 is disposed at one end of the knife rod 100, the driving member 700 is movably disposed on the rod handle 600, and the driving member 700 is in driving connection with the operating end of the guide wire 400, such that the driving member 700 drives the guide wire 400 to drive the pushing member 300 to move in the length direction of the knife rod 100 and to push the blade 200 to be exposed from the opening of the blade slot 110.

In order to facilitate operation, as shown in FIGS. 3-7 and FIGS. 10-14, in this embodiment, the rod handle 600 and the driving member 700 are disposed at one end of the knife rod 100, and the driving member 700 is movably disposed relative to the rod handle 600, such that the driving member 700 can be manually operated, and the guide wire 400 can accordingly pull the pushing member 300 to push the blade 200 to be exposed and tilted upwards from the opening of the blade slot 110; and of course, the driving member 700 can also be designed to be automatic, and a driving motor is mounted on the rod handle 600 to automatically drive the guide wire 400 to pull the pushing member 300 through the driving motor to push the blade 200 to be exposed from the opening of the blade slot 110.

In one embodiment, as shown in FIGS. 3-7, the driving member 700 includes a rotating member 710, the rotating member 710 is in threaded connection with the rod handle 600, the rotating member 710 is connected to the operating end of the guide wire 400, a threaded hole 320 is formed on the pushing member 300 in a length direction, one end of the guide wire 400 is threadedly connected in the threaded hole 320, and the pushing member 300 is inserted into the hollow cavity 120 of the knife rod 100 in a non-rotational manner, such that the guide wire 400 is driven to bring the pushing member 300 to move by rotating the rotating member 710.

Figure 7:
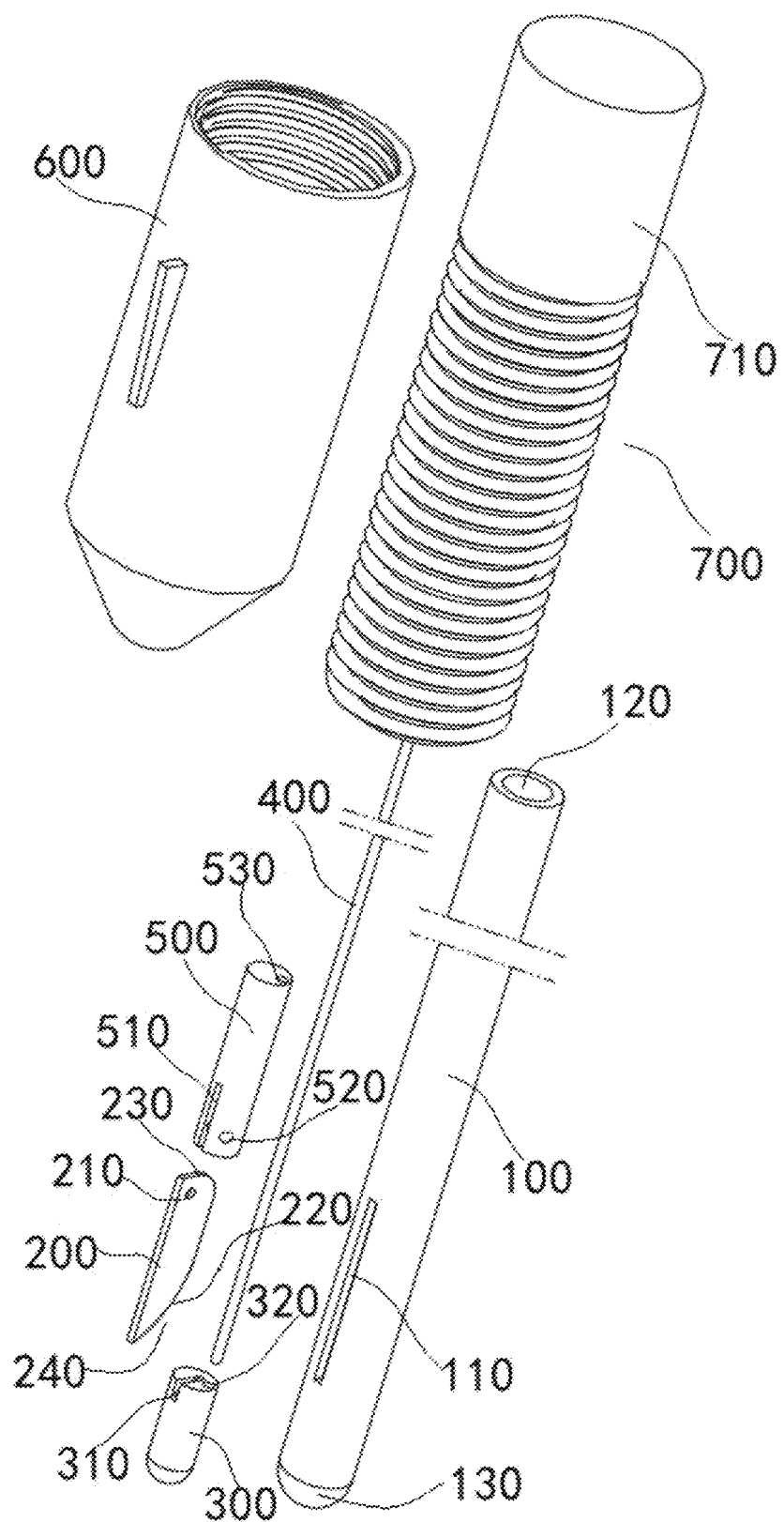
FIG. 7 is a structural exploded view of a pet intraurethral incision knife according to an implementation mode of an embodiment in the present disclosure.
Figure 8:
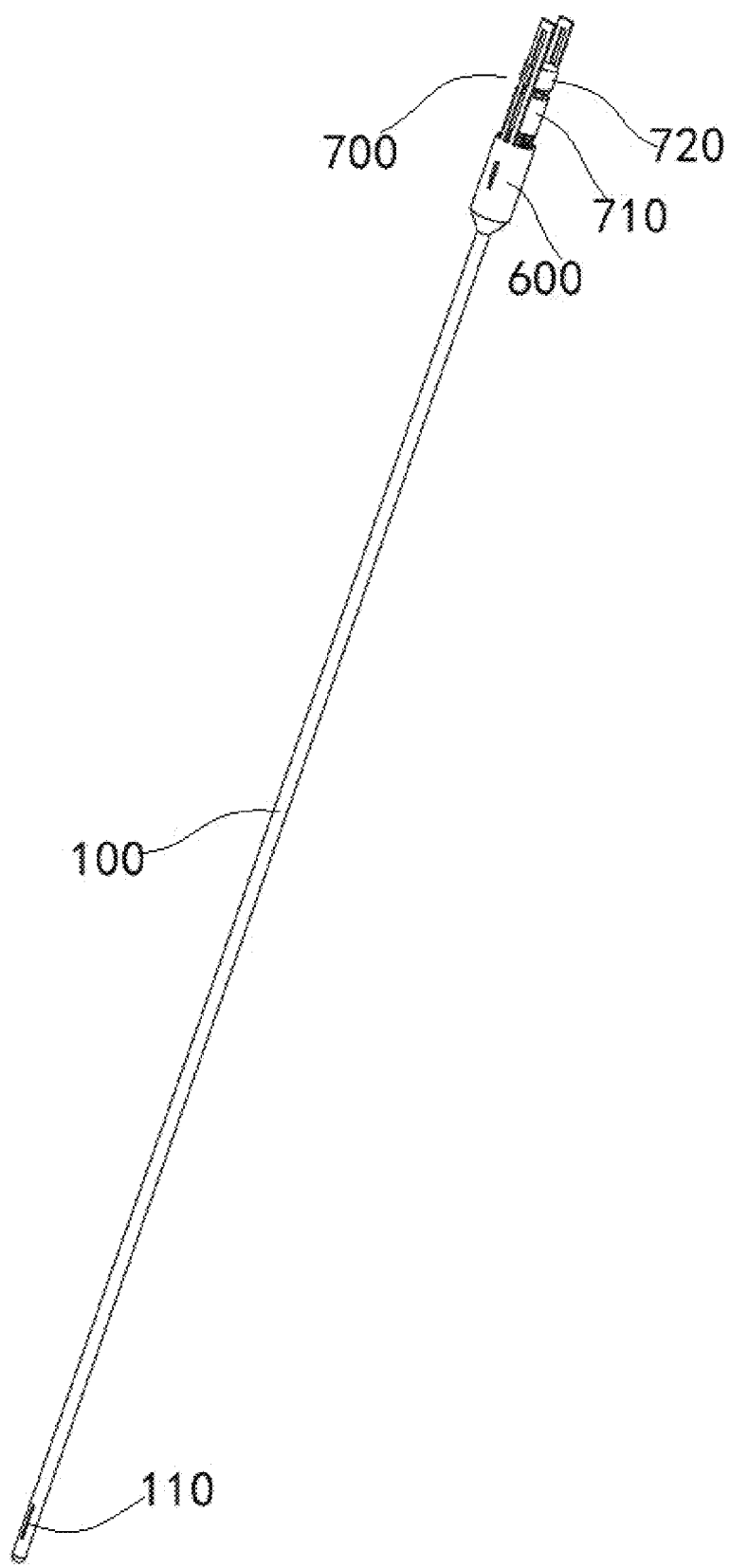
FIG. 8 is a structural schematic diagram of a pet intraurethral incision knife in a retracted state according to another implementation mode of an embodiment in the present disclosure.
Figure 9:
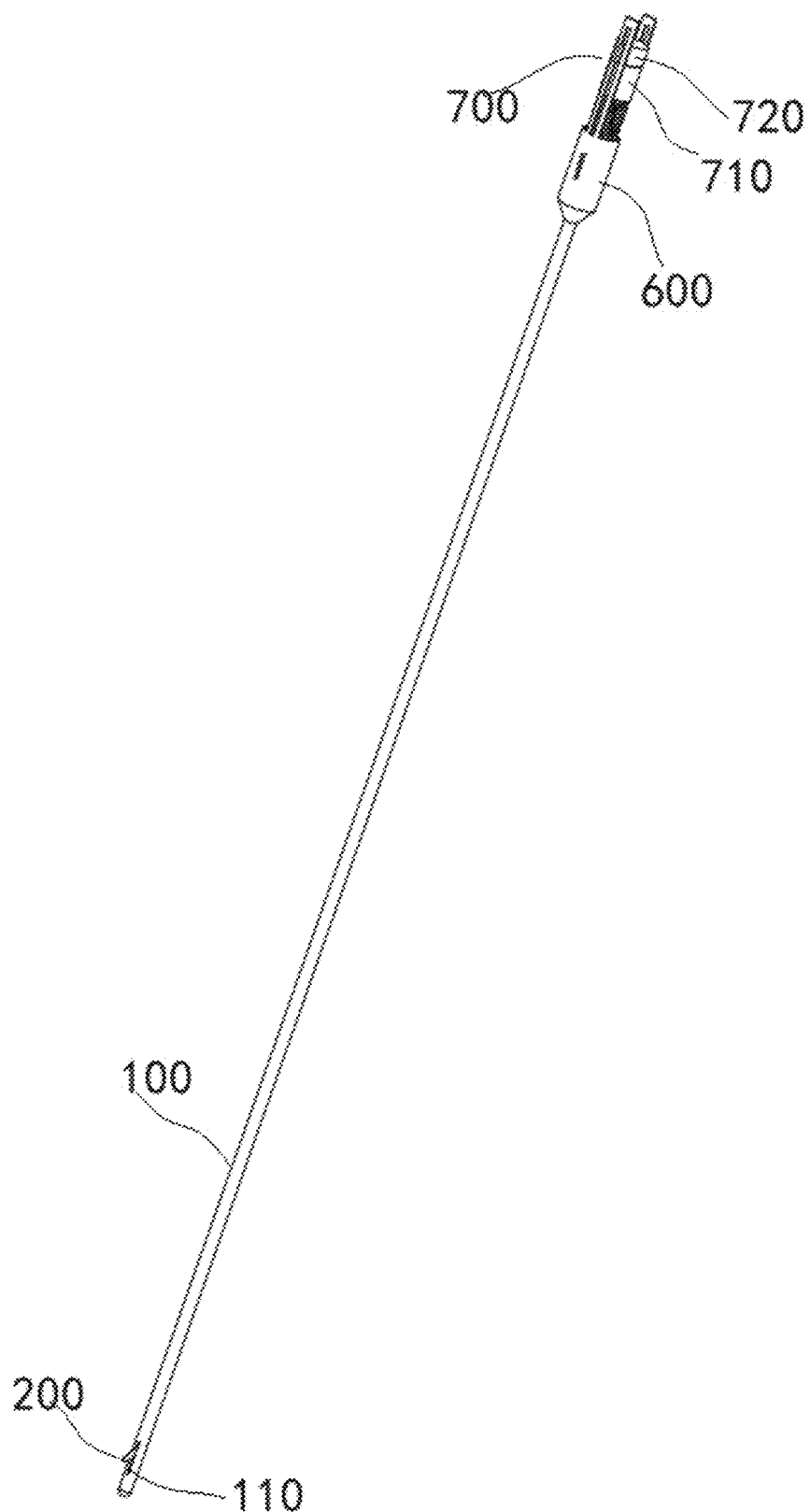
FIG. 9 is a structural schematic diagram of a pet intraurethral incision knife in an exposed state according to another implementation mode of an embodiment in the present disclosure.
Figure 10:
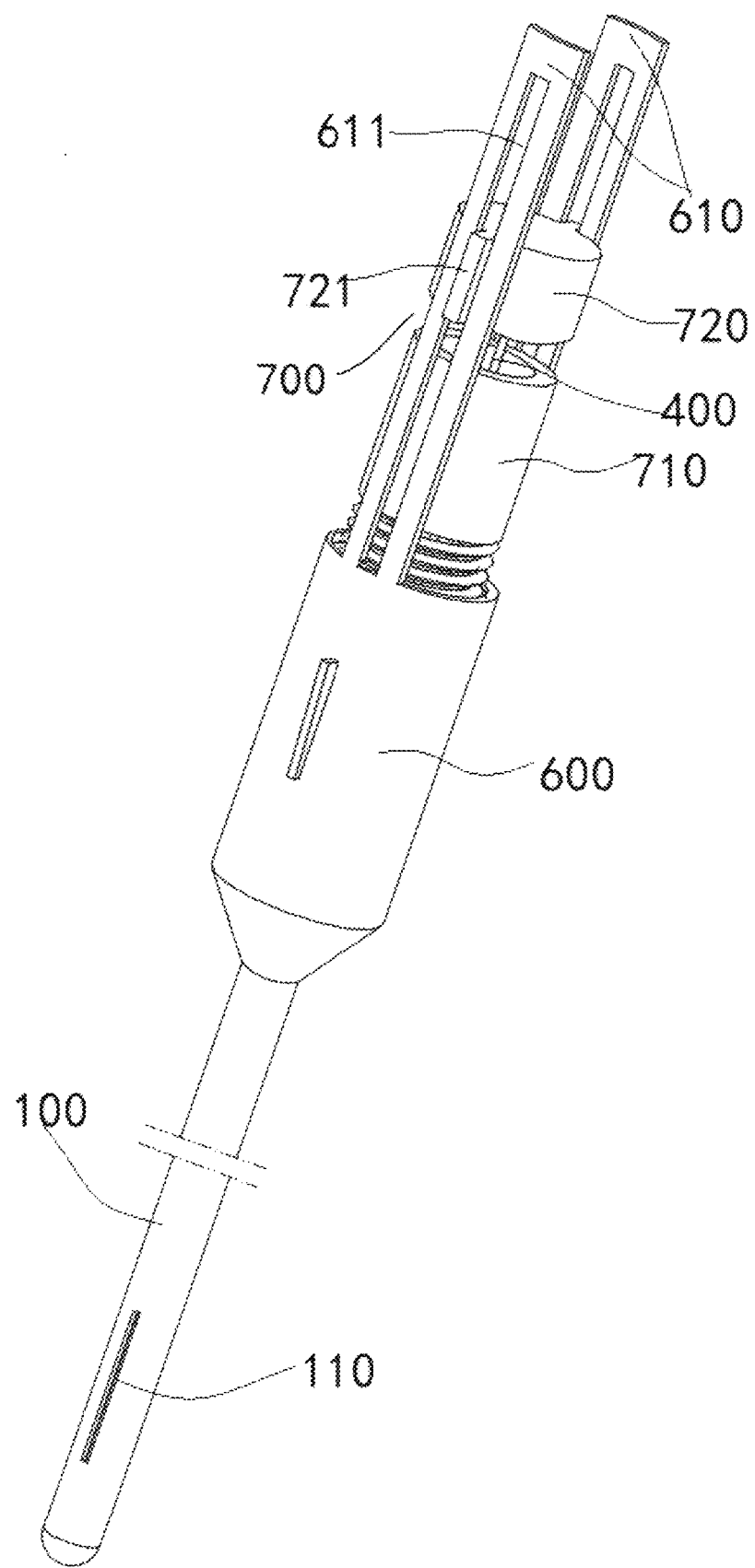
FIG. 10 is a simplified schematic diagram of a pet intraurethral incision knife in a retracted state according to another implementation mode of an embodiment in the present disclosure.
Figure 11:
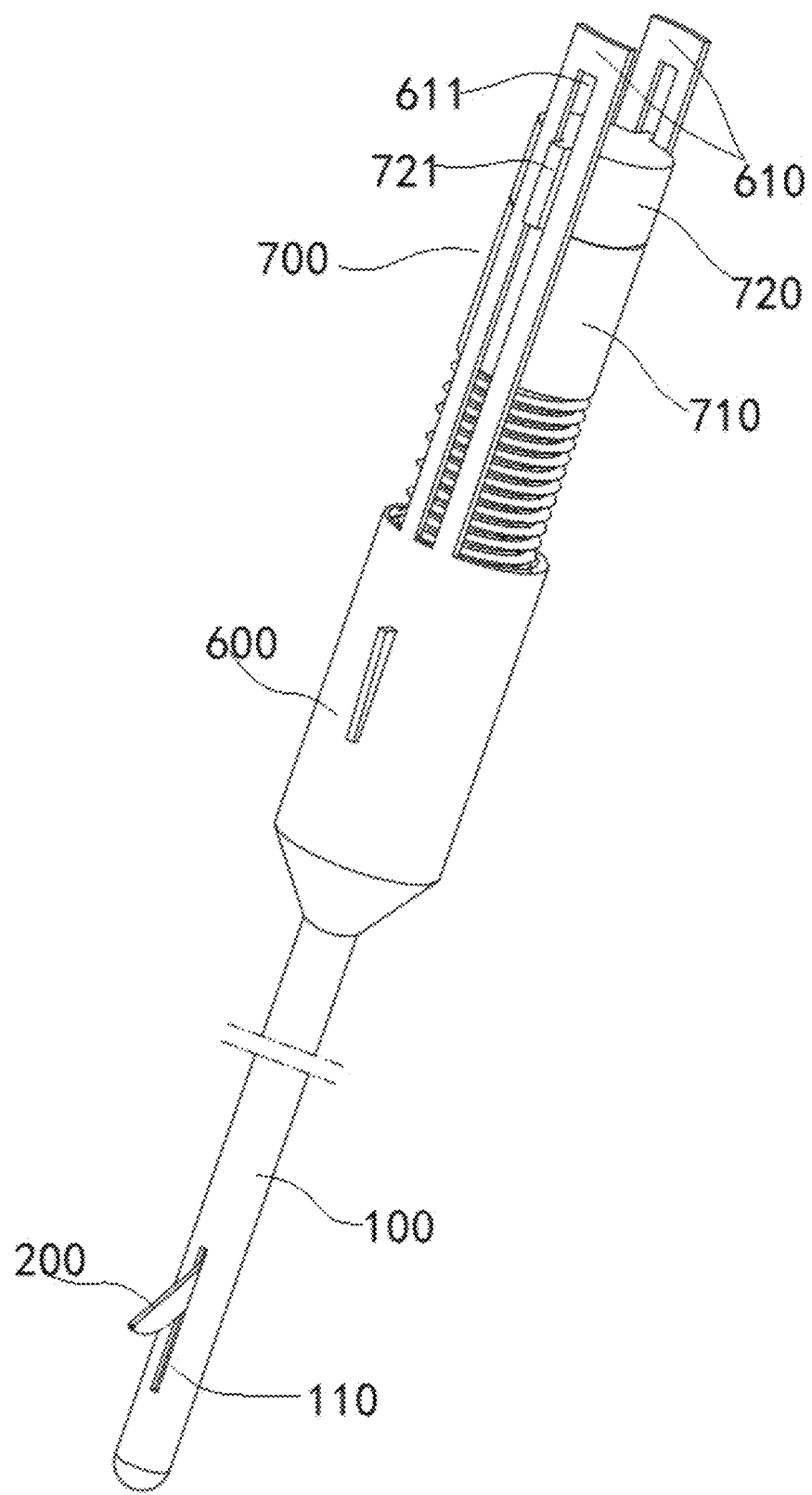
FIG. 11 is a simplified schematic diagram of a pet intraurethral incision knife in an exposed state according to another implementation mode of an embodiment in the present disclosure.

As shown in FIGS. 5-7, the rotating member 710 and the rod handle 600 are sleeved with each other in a threaded connection manner, an internal thread is formed on an inner cavity of the rod handle 600, an external thread is formed on an outer peripheral surface of the rotating member 710, the rotating member 710 is inserted into the inner cavity of the rod handle 600 in a threaded connection manner, the operating end of the guide wire 400 passes through the inner cavity of the rod handle 600 and is fixedly connected to the rotating member 710, the pushing member 300 is roughly a cylinder, and the threaded hole 320 is disposed at an eccentric position of the pushing member 300 close to one end of the blade 200, and an external thread is formed on an outer peripheral surface of one end of the guide wire 400, such that the guide wire 400 can be driven to rotate by rotating the rotating member 710; and since the pushing member 300 is in threaded connection with one end of the guide wire 400 in an eccentric state, the pushing member 300 cannot rotate in the hollow cavity 120 of the knife rod 100, such that when the rotating member 710 and the guide wire 400 rotate, the pushing member 300 moves in the hollow cavity 120 in the length direction of the knife rod 100 and pushes the blade 200 to be exposed and tilted upwards from the opening of the blade slot 110.

In another embodiment, as shown in FIGS. 10-14, the driving member 700 includes a sliding block 720, the sliding block 720 is connected to the operating end of the guide wire 400, a sliding portion 721 is disposed on at least one side of the sliding block 720, a guide slot 611 is formed on the rod handle 600 in a length direction thereof, and the sliding portion 721 is slidably disposed in the guide slot 611, such that the guide wire 400 can be driven to push the pushing member 300 to move and to push the blade 200 to be exposed and tilted upwards from the opening of the blade slot 110 by manually pushing and pulling the sliding block 720.

Figure 14:
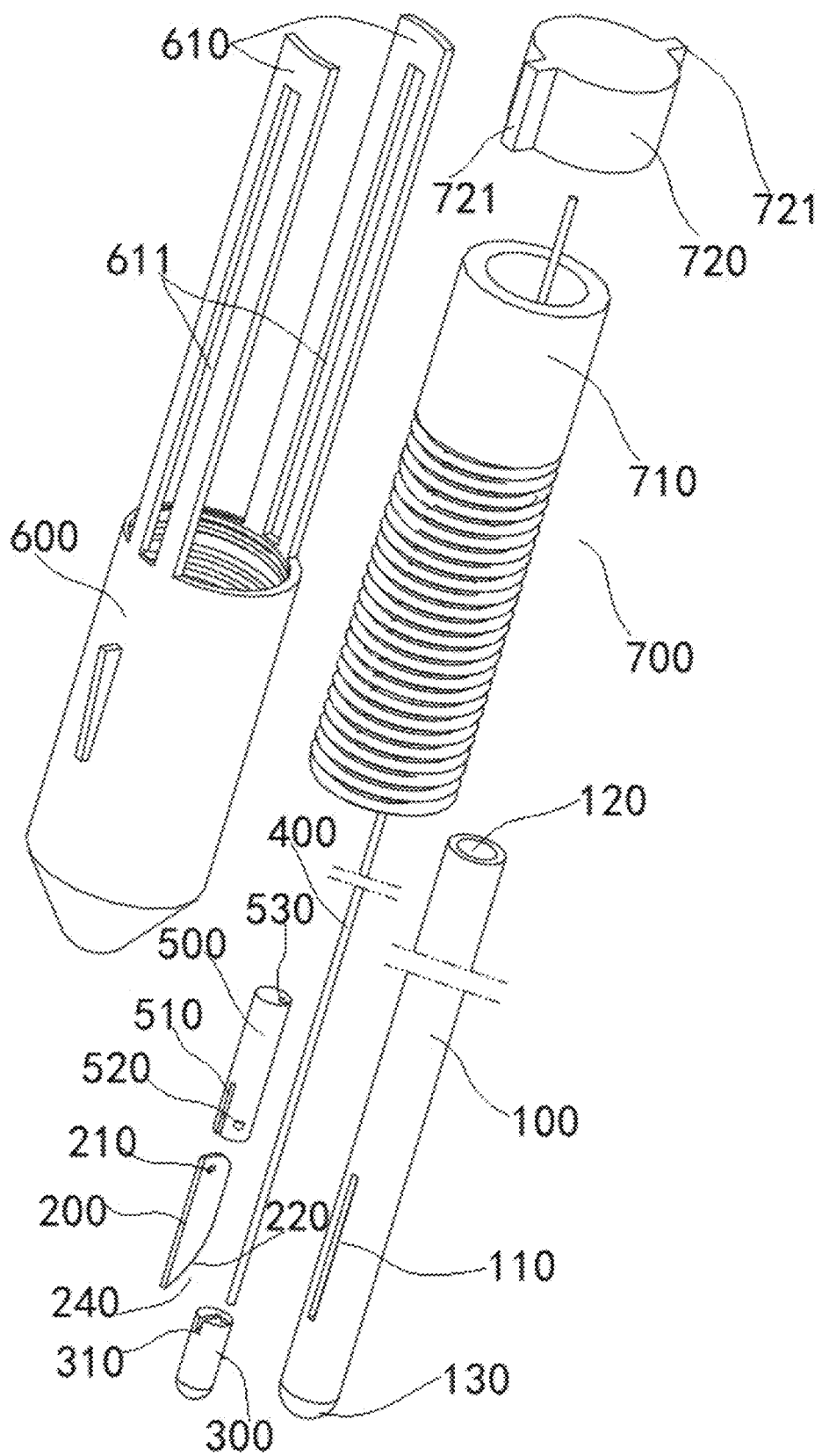
FIG. 14 is a structural exploded view of a pet intraurethral incision knife according to another implementation mode of an embodiment in the present disclosure.

Specifically, as shown in FIGS. 12-14, two opposite sides of the sliding block 720 are protruded outwards to form sliding portions 721, two opposite sides of the rod handle 600 are respectively extended to one end away from the knife rod 100 to form guide walls 610, one guide slot 611 is formed on each of the guide walls 610 in a length direction thereof, and the rod handle 600 and the guide walls 610 can be integrally made of elastic material; and in the assembly process, in order to make the two sliding portions 721 of the sliding block 720 slidably fitted into the guide slots 611 of the two guide walls 610, respectively, the operating end of the guide wire 400 passes through the inner cavity of the rod handle 600 and is fixedly connected to the sliding block 720, such that the guide wire 400 can be driven to push the pushing member 300 to move and to push the blade 200 to be exposed and tilted upwards from the opening of the blade slot 110 by manually pushing and pulling the sliding block 720.

In another embodiment, as shown in FIGS. 10-14, the driving member 700 includes the rotating member 710 and the sliding block 720, the sliding block 720 is connected to the operating end of the guide wire 400, the sliding portion 721 is disposed on at least one side of the sliding block 720, the guide slot 611 is formed on the rod handle 600 in a length direction thereof, the sliding portion 721 is slidably disposed in the guide slot 611, the rotating member 710 is in threaded connection with and the rod handle 600, and the rotating member 710 is connected to the sliding block 720, such that the guide wire 400 can be driven to push the pushing member 300 to move and to push the blade 200 to be exposed and tilted upwards from the opening of the blade slot 110 by rotating the rotating member 710 to push the sliding block 720 to slide.

Specifically, as shown in FIGS. 12-14, two opposite sides of the sliding block 720 are protruded outwards to form sliding portions 721, two opposite sides of the rod handle 600 are respectively extended to one end away from the knife rod 100 to form guide walls 610, one guide slot 611 is formed on each of the guide walls 610 in a length direction thereof, and the rod handle 600 and the guide walls 610 can be integrally made of elastic material; and in the assembly process, in order to make the two sliding portions 721 of the sliding block 720 slidably fitted into the guide slots 611 of the two guide walls 610, respectively, the rotating member 710 is disposed between the rod handle 600 and the sliding block 720, the rotating member 710 and the rod handle 600 are sleeved with each other in a threaded connection manner, the internal thread is formed on the inner cavity of the rod handle 600, the external thread is formed on the outer peripheral surface of the rotating member 710, the rotating member 710 is inserted into the inner cavity of the rod handle 600 in a threaded connection manner, one end of the rotating member 710 is abutted against with the one end of the sliding block 720, the operating end of the guide wire 400 passes through the inner cavity of the rod handle 600 and an inner cavity of the rotating member 710, and is fixedly connected to the sliding block 720, in this way, the rotating member 710 can be extended outwards relative to the rod handle 600 and the sliding block 720 can be pushed to slide in a direction away from the rod handle 600 manually rotating the rotating member 710, such that the guide wire 400 can be driven to push the pushing member 300 to move and to push the blade 200 to be exposed and tilted upwards from the opening of the blade slot 110, and the mode of pushing the blade 200 to be tilted upwards in a threaded rotation manner is easy to control the height of the blade 200 to be tilted upwards, featuring simple structural design and more stable and reliable.

Figure 15:
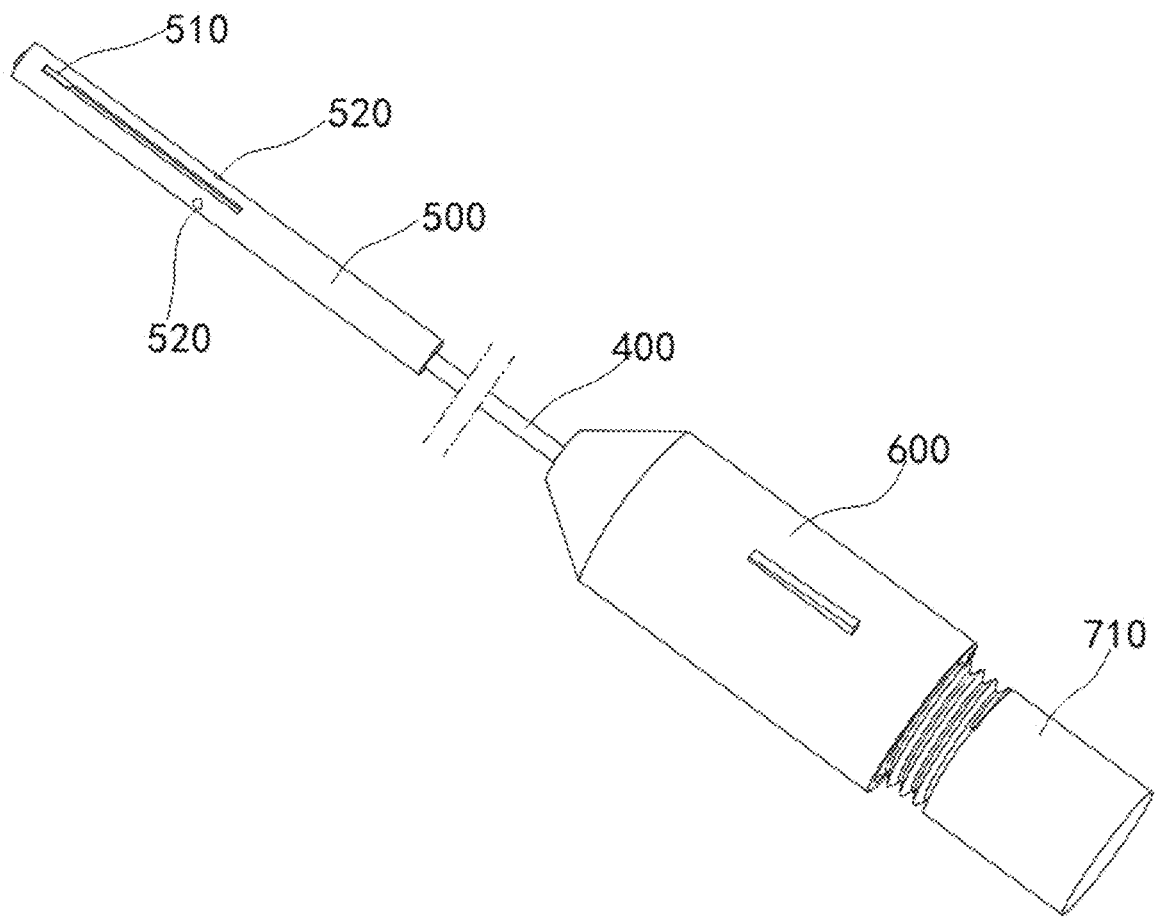
FIG. 15 is a simplified schematic diagram of a pet intraurethral incision knife in a retracted state according to another implementation mode of an embodiment in the present disclosure.
Figure 16:
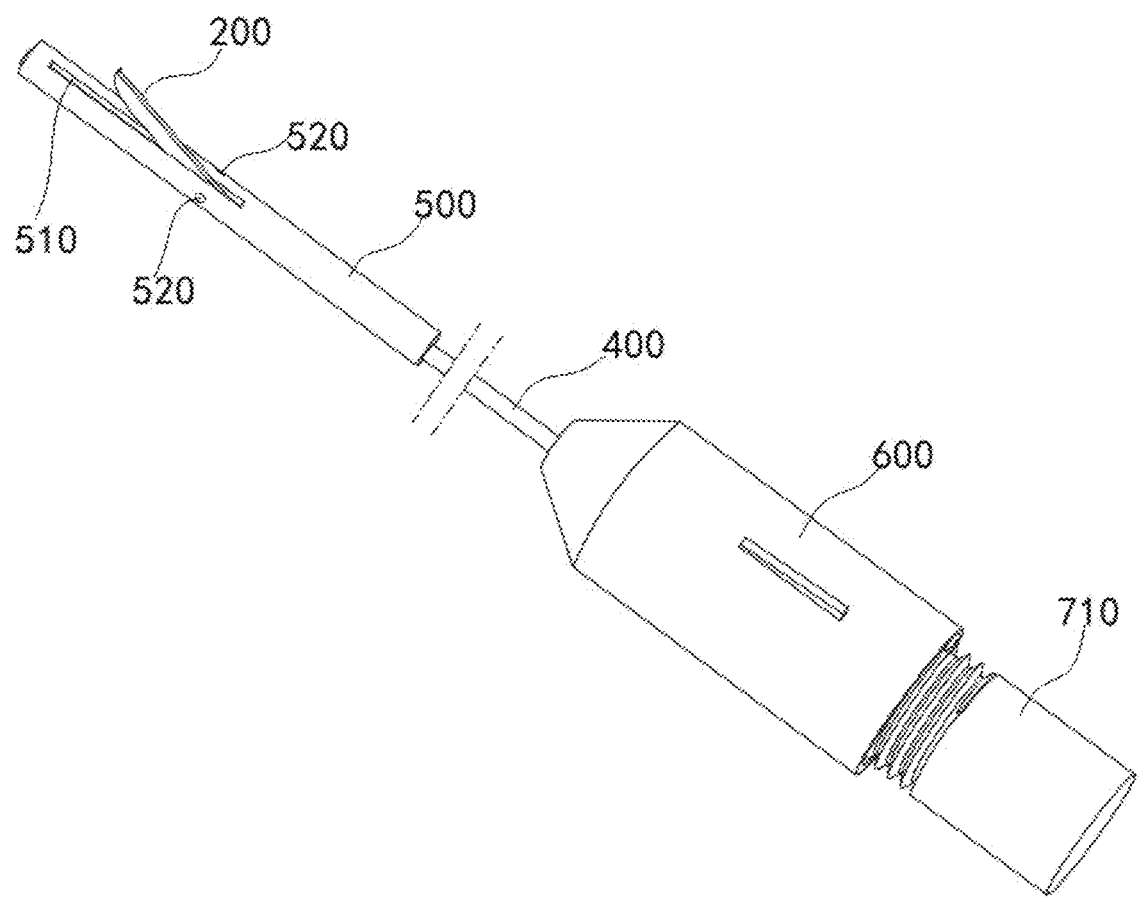
FIG. 16 is a simplified schematic diagram of a pet intraurethral incision knife in an exposed state according to another implementation mode of an embodiment in the present disclosure.
Figure 17:
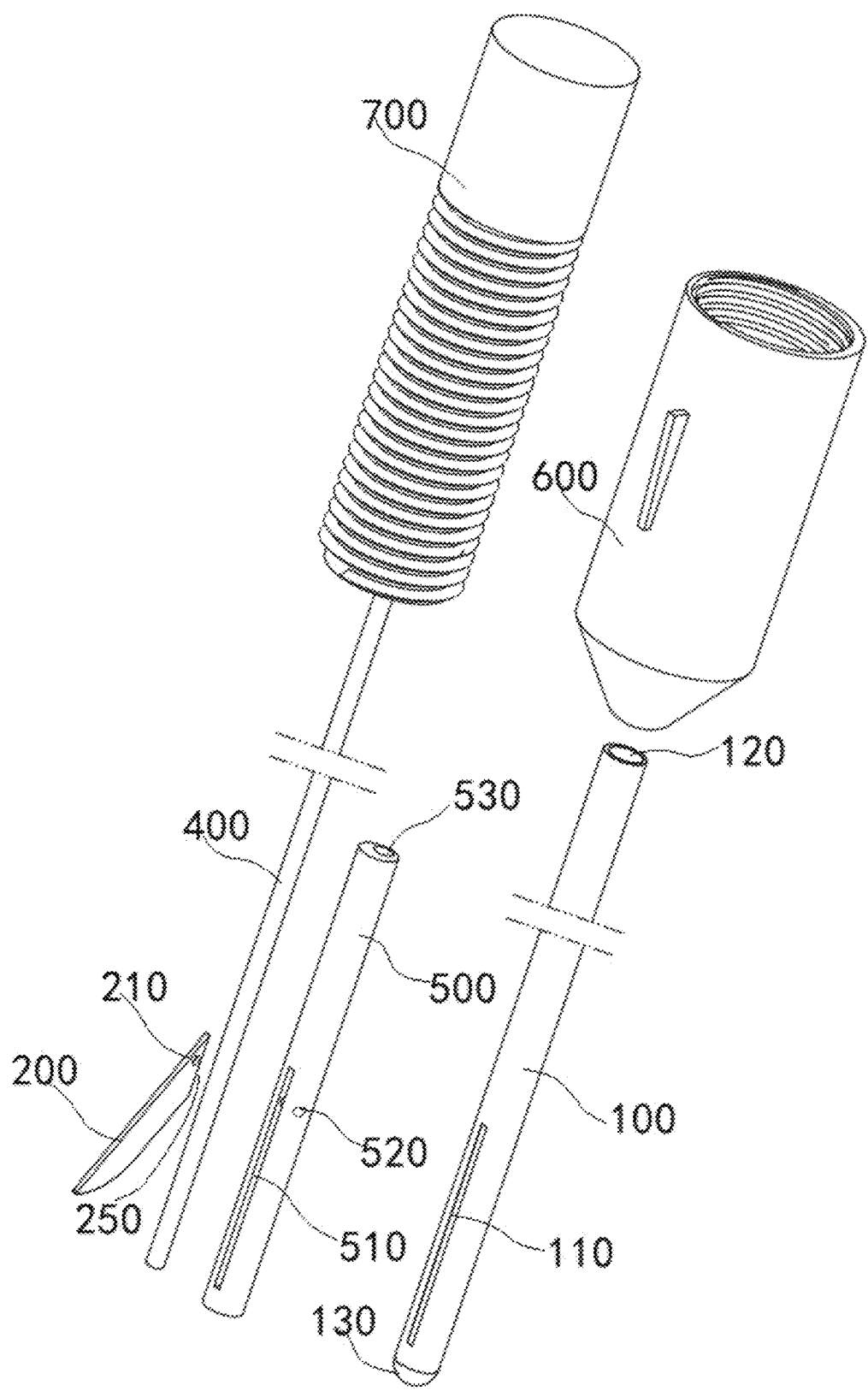
FIG. 17 is a structural exploded view of a pet intraurethral incision knife according to another implementation mode of an embodiment in the present disclosure.

In another embodiment, as shown in FIGS. 15-17, this embodiment is different from the embodiment shown in FIGS. 7-14. With reference to FIG. 17, in this embodiment, the pushing member 300 is omitted, and an inclined surface 250 is disposed at the edge of one end of the blade 200; when the blade 200 is in the exposed state, the blade 200 is abutted against one end of the guide wire 400 through the inclined surface 250 to support the blade 200 for positioning; specifically, when the blade 200 is in the retracted state, the blade 200 is retracted inside the blade slot 110, a length direction of the blade 200 is parallel to a longitudinal axis of the knife rod 100, and the inclined surface 250 is inclined to the longitudinal axis of the knife rod 100; and when the blade 200 is in the exposed state, the other end of the blade 200 is exposed from the opening of the blade slot 110, the length direction of the blade 200 is inclined to the longitudinal axis of the knife rod 100, and the inclined surface 250 is parallel to the longitudinal axis of the knife rod 100, such that the blade 200 is abutted against a peripheral wall of one side of the guide wire 400 through the inclined surface 250, and the blade 200 is supported for positioning, thereby preventing the blade 200 from swinging during surgical cutting to affect the cutting effect.

Further, as shown in FIGS. 15-17, the pet intraurethral incision knife further includes the mounting rod 500, the mounting groove 510 is formed on one side of the mounting rod 500, the mounting groove 510 is disposed correspondingly to the blade slot 110, the mounting holes 520 are formed on two opposite side walls of the mounting groove 510, and the through hole 210 is formed on one end of the blade 200, such that the blade 200 is inserted into the mounting groove 510 and is inserted into the through hole 210 of the blade 200 through the pivot shaft, and two ends of the pivot shafts are respectively inserted into two mounting holes 520 to make the blade 200 capable of being rotationally mounted, the mounting rod 500 is then inserted into the hollow cavity 120 of the knife rod 100 to make the mounting groove 510 of the mounting rod 500 disposed correspondingly to the blade slot, where the mounting rod 500 is a cylindrical rod structure; in the assembly process, the blade 200 is first inserted into the mounting groove 510, the pivot shaft is then inserted into the mounting holes 520 on the two opposite side walls of the mounting groove 510 and the through hole 210, the mounting rod 500 is inserted into the hollow cavity 120 of the knife rod 100, and the mounting groove 510 is disposed correspondingly to the blade slot 110, the blade 200 is thus rotationally mounted inside the blade slot 110, and finally an opening of the hollow cavity 120 of the knife rod 100 is covered by the end cap 130; where the mounting rod 500 and the inner wall of the hollow cavity 120 of the knife rod 100 can be bonded and fixed with glue, or the inner wall of the knife rod 100 can be contracted by means of a hot melting process to be tightly fitted and fixed with the mounting rod 500, featuring a simple and compact structural design, facilitating production and assembly, and effectively improving the stability and reliability of the structural design; and since the knife rod 100 is a flexible rod structure, and in this embodiment, the blade 200 is mounted by inserting the mounting rod 500 into the knife rod 100, which effectively improves the stability, reliability and seclusion of a mounting structure of the blade 200.

In this embodiment, as shown in FIGS. 15-17, the penetrating hole 530 is formed inside the mounting rod 500 in a length direction thereof, the penetrating hole 530 is communicated with the bottom of the mounting groove 510, and one end of the guide wire 400 is movably inserted into the penetrating hole 530; when the blade 200 is in the retracted state, the blade 200 at least partially passes through the bottom of the mounting groove 510 and is abutted against the guide wire 400 inside the penetrating hole 530, such that the guide wire 400 can push the blade 200 to rotate and to be exposed from the opening of the blade slot 110, in this way, the operating end drives one end of the guide wire 400 to push the blade 200 to rotate and to be exposed from the opening of the blade slot 110; in addition, the embodiment shown in FIGS. 15-17 has roughly the same structural principles as the rod handle and the driving member of the embodiment shown in FIG. 7 and FIG. 14, and reference can be made to the detailed description and introduction of the rod handle and the driving member according to the above embodiments, which will not be described in detail herein.

In the experimental tests, pet cats were used to test the surgical cutting effect of the pet intraurethral incision knife in the present disclosure. Experiments were performed on three breeds of pet cats in four age groups, the four age groups were cats aged one year, two years, three years and four years and were denoted as a, b, c and d, respectively, and the three breeds of pet cats were Garfield, Chartreux and Ragdoll and were denoted as X, Y and Z, respectively, a total of 12 groups of experiments were performed and were denoted as Xa, Xb, Xc, Xd, Ya, Yb, Yc, Yd, Za, Zb, Zc and Zd, respectively, and ten pet cats were included in each group, involving a total of 120 pet cats. The pet intraurethral incision knife in the present disclosure was used to perform surgical cutting of urethras of the pet cats. After half a year of postoperative observation, the final experimental results showed that symptoms of urinary retention of each group of pet cats were completely cured without any sequelae. After many experiments, the pet doctors concerned said that, compared with the prior art, the pet intraurethral incision knife in the present disclosure is very convenient to use, and reduces the difficulty of surgical incision, proving better effect in cutting the narrow blocking parts of the urethras of the pet cats.

From the above description, it can be seen that the above-mentioned embodiments of the present disclosure achieve the following technical effects:

It can be seen that the pet intraurethral incision knife provided in this embodiment includes the knife rod 100, the blade 200, and the guide wire 400, the blade slot 110 is formed on one side of the knife rod 100, the hollow cavity 120 is formed inside the knife rod 100 in the length direction, the hollow cavity 120 is communicated with the bottom of the blade slot 110, the blade 200 can be rotationally retracted inside the blade slot 110, the blade 200 has the retracted state and the exposed state relative to the blade slot 110, one end of the guide wire 400 is abutted against the edge of one end of the blade 200, and the other end of the guide wire 400 passes through the hollow cavity 120 and forms the operating end at one end of the knife rod 100, such that the operating end drives one end of the guide wire 400 to push the blade 200 to rotate and to be exposed from the opening of the blade slot 110, and the blade 200 is switched from the retracted state to the exposed state, in this way, the blade 200 can be hidden and stored inside the blade slot 110 before the pet intraurethral incision knife is inserted into the pet urethra to prevent the blade 200 from scratching normal parts of the pet urethra, and the knife rod 100 can be inserted into the pet urethra more smoothly; and when the blade 200 reaches the narrow blocking part of the pet urethra, the guide wire 400 is driven by the operating end to push the blade 200 to be exposed from the opening of the blade slot 110 and perform surgical cutting on the narrow blocking part of the pet urethra. Therefore, the pet intraurethral incision knife features simple structural design, makes the operation more convenient, thereby effectively reducing the difficulty of surgical operation and improving the efficiency of surgical cutting.

It should be understood that when an element is referred to as being "on" or "connected to" another element, it can be directly on the other element or directly connected to the other element or indirectly connected to the other element by an intervening element therebetween. On the contrary, when an element is referred to as being "directly on" or "directly connected to" another element, there are no intervening elements therebetween. Also, it should be noted that if directional indications (such as up, down, left, right, front, back, etc.) are involved in the embodiment of the present disclosure, the directional indications are only used to explain a relative position relationship, a movement condition and the like between various components under a certain posture (as shown in the accompanying drawings). If the specific posture changes, the directional indication changes accordingly.

The above are the preferred embodiments of the present disclosure. It should be noted that those skilled in the art can make several improvements and modifications without departing from the principles of the present disclosure, and these improvements and modifications may be regarded as the protection scope of the present disclosure.

What is claimed is:

1. A pet intraurethral incision knife, comprising:
   a knife rod, a blade slot being formed on one side of the knife rod, a hollow cavity being formed inside the knife rod in a length direction, and the hollow cavity being communicated with a bottom of the blade slot, and the knife rod is a flexible soft rod structure;
   a blade, the blade being rotationally retracted inside the blade slot, and the blade having a retracted state and an exposed state relative to the blade slot; and
   a guide wire, one end of the guide wire being abutted against an edge of one end of the blade, and the other end of the guide wire passing through the hollow cavity and forming an operating end at one end of the knife rod, such that the operating end drives one end of the guide wire to push the blade to rotate and to be exposed from an opening of the blade slot, and the blade can be switched from the retracted state to the exposed state.

2. The pet intraurethral incision knife according to claim 1, wherein an inclined surface is disposed at the edge of one end of the blade, and when the blade in the exposed state, the blade is abutted against one end of the guide wire through the inclined surface to support the blade for positioning.

3. The pet intraurethral incision knife according to claim 2, wherein when the blade is in the retracted state, the blade is retracted inside the blade slot, a length direction of the blade is parallel to a longitudinal axis of the knife rod, and the inclined surface is inclined to the longitudinal axis of the knife rod; and when the blade is in the exposed state, the other end of the blade is exposed from the opening of the blade slot, the length direction of the blade is inclined to the longitudinal axis of the knife rod, and the inclined surface is parallel to the longitudinal axis of the knife rod.

4. The pet intraurethral incision knife according to claim 1, wherein the blade slot is disposed in a way of extending in the length direction of the knife rod, one end of the blade can be rotationally mounted inside the blade slot through a pivot shaft, and the pivot shaft is extended in a width direction of the blade slot.

5. The pet intraurethral incision knife according to claim 4, further comprising a mounting rod, wherein a mounting groove is formed on one side of the mounting rod, the mounting groove is disposed correspondingly to the blade slot, and mounting holes are formed on two opposite side walls of the mounting groove, such that the blade is inserted into the mounting groove and is inserted into the through hole of the blade through the pivot shaft, two ends of the pivot shafts are respectively inserted into two mounting holes to make the blade capable of being rotationally mounted, and the mounting rod is then inserted into the hollow cavity of the knife rod to make the mounting groove of the mounting rod disposed correspondingly to the blade slot.

6. The pet intraurethral incision knife according to claim 5, wherein a penetrating hole is formed inside the mounting rod in a length direction, the penetrating hole is communicated with a bottom of the mounting groove, and one end of the guide wire is movably inserted into the penetrating hole; and when the blade is in the retracted state, the blade at least partially passes through the bottom of the mounting groove and is abutted against the guide wire inside the penetrating hole, such that the guide wire can push the blade to rotate and to be exposed from the opening of the blade slot.

7. The pet intraurethral incision knife according to claim 1, further comprising a pushing member, the pushing member is movably disposed inside the hollow cavity of the knife rod, and one end of the guide wire is connected to the pushing member, such that one end of the guide wire is abutted against the edge of one end of the blade through the pushing member, and the operating end drives the guide wire to drive the pushing member to push the blade to rotate and to be exposed from the opening of the blade slot.

8. The pet intraurethral incision knife according to claim 7, wherein the blade slot is disposed in a way of extending in the length direction of the knife rod, the other end of the blade can be rotationally mounted inside the blade slot through the pivot shaft, and a pivot axis of the pivot shaft is extended in the width direction of the blade slot.

9. The pet intraurethral incision knife according to claim 8, further comprising the mounting rod, the mounting groove is formed on a side of the mounting rod facing the opening of the blade slot in a length direction, such that the other end of the blade can be rotationally mounted inside the mounting groove through the pivot shaft, and the mounting rod is inserted into the hollow cavity of the knife rod to make the blade rotationally mounted inside the blade slot.

10. The pet intraurethral incision knife according to claim 8, further comprising the mounting rod, the mounting groove is formed on the side of the mounting rod facing the opening of the blade slot in the length direction, the other end of the blade can be rotationally mounted inside the mounting groove through the pivot shaft, the penetrating hole is formed inside the mounting rod in the length direction, the penetrating hole is communicated with the bottom of the mounting groove, the pushing member is movably disposed inside the penetrating hole, and one end of the guide wire is inserted into the penetrating hole and is connected to the pushing member, such that the mounting rod is inserted into the hollow cavity of the knife rod to make the blade rotationally mounted inside the blade slot; and when the blade is in the retracted state, the blade at least partially passes through the bottom of the mounting groove and is abutted against the pushing member inside the penetrating hole, such that the guide wire can push the blade through the pushing member to rotate and to be exposed from the opening of the blade slot.

11. The pet intraurethral incision knife according to claim 7, wherein a guide surface is disposed at the edge of one end of the blade, a guide groove is formed on one end of the pushing member close to the blade, and one end of the blade is movably disposed in the guide groove through the guide surface, such that the pushing member is abutted against the guide surface through the guide groove and pushes the blade to rotate and to be exposed from the opening of the blade slot.

12. The pet intraurethral incision knife according to claim 7, further comprising the rod handle and the driving member, and the rod handle is disposed at one end of the knife rod; and the driving member comprises the rotating member, the rotating member is in threaded connection with the rod handle, and the rotating member is connected to the operating end of the guide wire, a threaded hole is formed on the pushing member in a length direction, one end of the guide wire is threadedly connected in the threaded hole, and the pushing member is inserted into the hollow cavity of the knife rod in a non-rotational manner, such that the guide wire is driven to bring the pushing member to move by rotating the rotating member; or further comprising the rod handle and the driving member, and the rod handle is disposed at one end of the knife rod; and the driving member comprises a sliding block, the sliding block is connected to the operating end of the guide wire, the sliding portion is disposed on at least one side of the sliding block, the guide slot is formed on the rod handle in the length direction, and the sliding portion is slidably disposed in the guide slot, such that the guide wire is driven to bring the pushing member to move by pushing and pulling the sliding block; or further comprising the rod handle and the driving member, and the rod handle is disposed at one end of the knife rod; and the driving member comprises the rotating member and the sliding block, the sliding block is connected to the operating end of the guide wire, the sliding portion is disposed on at least one side of the sliding block, the guide slot is formed on the rod handle in the length direction, the sliding portion is slidably disposed in the guide slot, the rotating member is in threaded connection with the rod handle, and the rotating member is abutted against the sliding block, such that the sliding block can be driven to bring the pushing member to move by rotating the rotating member to push the sliding block to slide.

13. The pet intraurethral incision knife according to claim 1, further comprising a rod handle and a driving member, wherein the rod handle is disposed at one end of the knife rod, the driving member is movably disposed on the rod handle, and the driving member is in driving connection with the operating end of the guide wire, such that the driving member drives the guide wire to push the blade to be exposed from the opening of the blade slot.

14. The pet intraurethral incision knife according to claim 13, wherein the driving member comprises a rotating member, the rotating member is in threaded connection with the rod handle, and the rotating member is connected to the operating end of the guide wire, such that the guide wire is driven to push the blade to rotate and to be exposed from the opening of the blade slot by rotating the rotating member; or
    the driving member comprises a sliding block, the sliding block is connected to the operating end of the guide wire, a sliding portion is disposed on at least one side of the sliding block, a guide slot is formed on the rod handle in a length direction, and the sliding portion is slidably disposed in the guide slot, such that the guide wire can be driven to push the blade to be exposed from the opening of the blade slot by manually pushing and pulling the sliding block.

* * * * *